US012579638B2

(12) United States Patent
Machii

(10) Patent No.: US 12,579,638 B2
(45) Date of Patent: Mar. 17, 2026

(54) IMAGE PROCESSING DEVICE, IMAGE PROCESSING METHOD, AND IMAGE PROCESSING PROGRAM FOR PERFORMING DETERMINATION REGARDING DIAGNOSIS OF LESION ON BASIS OF SYNTHESIZED TWO-DIMENSIONAL IMAGE AND PRIORITY TARGET REGION

(71) Applicant: FUJIFILM CORPORATION, Tokyo (JP)

(72) Inventor: Yusuke Machii, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 325 days.

(21) Appl. No.: 17/822,138

(22) Filed: Aug. 25, 2022

(65) Prior Publication Data

US 2023/0095304 A1 Mar. 30, 2023

(30) Foreign Application Priority Data

Sep. 30, 2021 (JP) ................................. 2021-162030

(51) Int. Cl.
| | |
|---|---|
| *G06T 7/00* | (2017.01) |
| *A61B 6/02* | (2006.01) |
(Continued)

(52) U.S. Cl.
CPC ............ *G06T 7/0012* (2013.01); *A61B 6/025* (2013.01); *A61B 6/502* (2013.01); *G06T 3/40* (2013.01);
(Continued)

(58) Field of Classification Search
CPC ........... G06T 7/0012; G06T 3/40; G06T 7/60; G06T 11/006; G06T 2207/10112;
(Continued)

(56) References Cited

U.S. PATENT DOCUMENTS

| | | | | | |
|---|---|---|---|---|---|
| 9,805,507 | B2 * | 10/2017 | Chen | ...................... | G06T 19/003 |
| 11,334,994 | B2 * | 5/2022 | Kim | ......................... | G06N 3/08 |
(Continued)

FOREIGN PATENT DOCUMENTS

| | | |
|---|---|---|
| JP | 2015-506794 A | 3/2015 |
| KR | 10-2021-0095654 A | 8/2021 |
(Continued)

OTHER PUBLICATIONS

Agarwal et al., "Automatic mass detection in mammograms using deep convolutional neural networks," Journal of Medical Imaging 6(3), 031409 (Feb. 20, 2019). https://doi.org/10.1117/1.JMI.6.3.031409 (Year: 2019).*

(Continued)

Primary Examiner — Emily C Terrell
Assistant Examiner — Julia Z. Yao
(74) Attorney, Agent, or Firm — SOLARIS Intellectual Property Group, PLLC

(57) ABSTRACT

An image processing device includes at least one processor. The processor detects a specific structural pattern indicating a lesion candidate structure for a breast in a series of a plurality of projection images obtained by performing tomosynthesis imaging on the breast or in a plurality of tomographic images obtained from the plurality of projection images, synthesizes the plurality of tomographic images to generate a synthesized two-dimensional image, specifies a priority target region, in which the specific structural pattern is present, in the synthesized two-dimensional image, and performs determination regarding a diagnosis of a lesion on the basis of the synthesized two-dimensional image and the priority target region.

20 Claims, 20 Drawing Sheets

(51) Int. Cl.

| | |
|---|---|
| *A61B 6/50* | (2024.01) |
| *G06T 3/40* | (2024.01) |
| *G06T 7/60* | (2017.01) |
| *G06T 11/00* | (2026.01) |
| *G06V 10/22* | (2022.01) |
| *G06V 10/764* | (2022.01) |
| *G06V 10/774* | (2022.01) |

(52) U.S. Cl.
CPC .............. *G06T 7/60* (2013.01); *G06T 11/006* (2013.01); *G06V 10/22* (2022.01); *G06V 10/764* (2022.01); *G06V 10/774* (2022.01); *G06T 2207/10112* (2013.01); *G06T 2207/20081* (2013.01); *G06T 2207/30068* (2013.01); *G06T 2207/30096* (2013.01); *G06V 2201/03* (2022.01)

(58) Field of Classification Search
CPC . G06T 2207/20081; G06T 2207/30068; G06T 2207/30096; G06T 2207/20084; A61B 6/025; A61B 6/502; A61B 6/463; A61B 6/468; A61B 6/5217; G06V 10/22; G06V 10/764; G06V 10/774; G06V 2201/03
See application file for complete search history.

(56) References Cited

U.S. PATENT DOCUMENTS

| | | |
|---|---|---|
| 2015/0052471 A1 | 2/2015 | Chen |
| 2016/0106388 A1 | 4/2016 | Homma et al. |
| 2018/0218495 A1* | 8/2018 | Ben-Ari ............... A61B 6/5258 |
| 2019/0236782 A1* | 8/2019 | Amit ...................... G06T 7/0016 |
| 2019/0287234 A1* | 9/2019 | Panda ..................... G06T 7/136 |
| 2020/0167920 A1 | 5/2020 | Hall et al. |
| 2020/0342589 A1* | 10/2020 | Heindl ................... G06T 7/143 |
| 2021/0113167 A1* | 4/2021 | Chui ................... A61B 6/5217 |
| 2021/0125334 A1* | 4/2021 | Lotter ................... A61B 6/502 |
| 2021/0174504 A1* | 6/2021 | Madabhushi .......... G16H 30/40 |
| 2022/0015731 A1* | 1/2022 | Liu ........................... G06T 5/73 |

FOREIGN PATENT DOCUMENTS

| | | |
|---|---|---|
| WO | 2014/192187 A1 | 12/2014 |
| WO | 2020/68767 A1 | 4/2020 |
| WO | 2021/81483 A1 | 4/2021 |

OTHER PUBLICATIONS

Ke et al. FIMIL: A high-throughput deep learning model for abnormality detection with weak annotation in microscopy images. 2020. In Proceedings of Australasian Computer Science Week Multiconference (ACSW '20). ACM, Article 34, 1-6. https://doi.org/10.1145/3373017.3373051 (Year: 2020).*

English language translation of the following: Office action dated Feb. 4, 2025 from the JPO in a Japanese patent application No. 2021-162030 corresponding to the instant patent application. This office action translation is submitted now in order to supplement the understanding of the cited references which are being disclosed in the instant Information Disclosure Statement.

* cited by examiner

FIG. 6

```
        ┌──────────────────────┐
        │   LEARNING PROCESS   │
        │       START          │
        └──────────┬───────────┘
                   │
        ┌──────────┴───────────┐
        │ ACQUIRE TRAINING DATA │────S100
        └──────────┬───────────┘
                   │
        ┌──────────┴───────────┐
        │ TRAIN LESION DIAGNOSIS MODEL │────S102
        └──────────┬───────────┘
                   │
        ┌──────────┴───────────┐
        │        END           │
        └──────────────────────┘
```

FIG. 11

WEIGHT MAP

MULTIPLICATION

IMAGE PROCESSING DEVICE, IMAGE PROCESSING METHOD, AND IMAGE PROCESSING PROGRAM FOR PERFORMING DETERMINATION REGARDING DIAGNOSIS OF LESION ON BASIS OF SYNTHESIZED TWO-DIMENSIONAL IMAGE AND PRIORITY TARGET REGION

CROSS-REFERENCE TO RELATED APPLICATIONS

The present application claims priority under 35 U.S.C. § 119 to Japanese Patent Application No. 2021-162030 filed on Sep. 30, 2021. The above application is hereby expressly incorporated by reference, in its entirety, into the present application.

BACKGROUND

1. Technical Field

The present disclosure relates to an image processing device, an image processing method, and an image processing program.

2. Description of the Related Art

A doctor or the like performs a diagnosis of a lesion in a breast using a radiographic image obtained by irradiating the breast with radiation, and a technique for supporting the diagnosis by the doctor or the like is known. For example, WO2014/192187A discloses a technique in which a candidate for a disorder of the construction of mammary glands is extracted from an X-ray image of the breast by computer-aided diagnosis (CAD) and a lesion determination unit determines whether or not the candidate for the disorder of the construction of the mammary glands is a lesion on the basis of a feature amount of a region of interest.

SUMMARY

In the technique disclosed in WO2014/192187A, the accuracy of determining whether a structure is a lesion may not be sufficient. For example, in the technique described in WO2014/192187A, it may be difficult to determine whether or not a structure is a lesion in a case in which the structures of the mammary glands overlap.

The present disclosure has been made in view of the above circumstances, and an object of the present disclosure is to provide an image processing device, an image processing method, and an image processing program that can accurately perform determination regarding a diagnosis of a lesion of a breast.

In order to achieve the above object, according to a first aspect of the present disclosure, there is provided an image processing device comprising at least one processor. The processor detects a specific structural pattern indicating a lesion candidate structure for a breast in a series of a plurality of projection images obtained by performing tomosynthesis imaging on the breast or in a plurality of tomographic images obtained from the plurality of projection images, synthesizes the plurality of tomographic images to generate a synthesized two-dimensional image, specifies a priority target region, in which the specific structural pattern is present, in the synthesized two-dimensional image, and performs determination regarding a diagnosis of a lesion on the basis of the synthesized two-dimensional image and the priority target region.

According to a second aspect of the present disclosure, in the image processing device according to the first aspect, the processor may focus the determination regarding the diagnosis of the lesion more on the priority target region than on another region in the synthesized two-dimensional image.

According to a third aspect of the present disclosure, in the image processing device according to the first aspect or the second aspect, the processor may extract the priority target region from the synthesized two-dimensional image and perform the determination regarding the diagnosis of the lesion on the extracted priority target region.

According to a fourth aspect of the present disclosure, in the image processing device according to the third aspect, the processor may extract the priority target region on the basis of a condition corresponding to a type of the specific structural pattern.

According to a fifth aspect of the present disclosure, in the image processing device according to any one of the first to fourth aspects, the processor may detect the specific structural pattern for each type of the specific structural pattern.

According to a sixth aspect of the present disclosure, in the image processing device according to any one of the first to fifth aspects, the processor may specify a type of the specific structural pattern and specify the priority target region for each specified type.

According to a seventh aspect of the present disclosure, in the image processing device according to any one of the first to sixth aspects, the processor may specify a type of the specific structural pattern and perform the determination regarding the diagnosis of the lesion on the basis of the specified type and the priority target region.

According to an eighth aspect of the present disclosure, in the image processing device according to the seventh aspect, the processor may determine whether the lesion is benign or malignant as the determination regarding the diagnosis of the lesion.

According to a ninth aspect of the present disclosure, in the image processing device according to the seventh aspect, the processor may determine whether or not the specific structural pattern is a lesion as the determination regarding the diagnosis of the lesion.

According to a tenth aspect of the present disclosure, in the image processing device according to the seventh aspect, the processor may determine whether or not the lesion is malignant as the determination regarding the diagnosis of the lesion.

According to an eleventh aspect of the present disclosure, in the image processing device according to the seventh aspect, the processor may determine whether the specific structural pattern is a benign lesion, a malignant lesion, or a structure other than a lesion as the determination regarding the diagnosis of the lesion.

According to a twelfth aspect of the present disclosure, in the image processing device according to the seventh aspect, the processor may determine a degree of malignancy as the determination regarding the diagnosis of the lesion.

According to a thirteenth aspect of the present disclosure, in the image processing device according to any one of the first to twelfth aspects, the processor may specify a type of the specific structural pattern using a plurality of detectors that are provided for each type of the specific structural pattern and output, as a detection result, information indicating the specific structural pattern from the plurality of input projection images or from the plurality of input tomographic images.

According to a fourteenth aspect of the present disclosure, in the image processing device according to any one of the first to thirteenth aspects, the processor may detect the specific structural pattern using a detector generated by performing machine learning on a machine learning model with a geometrical structural pattern, a detector generated by performing machine learning on a mathematical model with simulation image data, or a detector generated by performing machine learning on a machine learning model using a radiographic image of the breast as training data.

According to a fifteenth aspect of the present disclosure, in the image processing device according to any one of the first to the fourteenth aspects, in a case in which a size of the breast included in the plurality of tomographic images is different from a size of the breast included in the synthesized two-dimensional image, the processor may perform a process of making the sizes equal to each other to specify the priority target region, in which the specific structural pattern is present, in the synthesized two-dimensional image.

According to a sixteenth aspect of the present disclosure, in the image processing device according to any one of the first to fifteenth aspects, a process of specifying the priority target region, in which the specific structural pattern is present, in the synthesized two-dimensional image may be incorporated into a process of synthesizing the plurality of tomographic images to generate the synthesized two-dimensional image.

Further, in order to achieve the above object, according to a seventeenth aspect of the present disclosure, there is provided an image processing method executed by a computer. The image processing method comprises: detecting a specific structural pattern indicating a lesion candidate structure for a breast in a series of a plurality of projection images obtained by performing tomosynthesis imaging on the breast or in a plurality of tomographic images obtained from the plurality of projection images; synthesizing the plurality of tomographic images to generate a synthesized two-dimensional image; specifying a priority target region, in which the specific structural pattern is present, in the synthesized two-dimensional image; and performing determination regarding a diagnosis of a lesion on the basis of the synthesized two-dimensional image and the priority target region.

Furthermore, in order to achieve the above object, according to an eighteenth aspect of the present disclosure, there is provided an image processing program that causes a computer to execute a process comprising: detecting a specific structural pattern indicating a lesion candidate structure for a breast in a series of a plurality of projection images obtained by performing tomosynthesis imaging on the breast or in a plurality of tomographic images obtained from the plurality of projection images; synthesizing the plurality of tomographic images to generate a synthesized two-dimensional image; specifying a priority target region, in which the specific structural pattern is present, in the synthesized two-dimensional image; and performing determination regarding a diagnosis of a lesion on the basis of the synthesized two-dimensional image and the priority target region.

According to the present disclosure, it is possible to accurately perform determination regarding a diagnosis of a lesion of a breast.

BRIEF DESCRIPTION OF THE DRAWINGS

Exemplary embodiments according to the technique of the present disclosure will be described in detail based on the following figures, wherein:

FIG. 6 is a diagram illustrating a convolution process, FIG. 11 is a diagram illustrating an example of a determination method by a lesion diagnosis determination unit according to the embodiment.

DETAILED DESCRIPTION

Hereinafter, an embodiment of the present disclosure will be described in detail with reference to the drawings. In addition, this embodiment does not limit the present disclosure.

Figure 1:
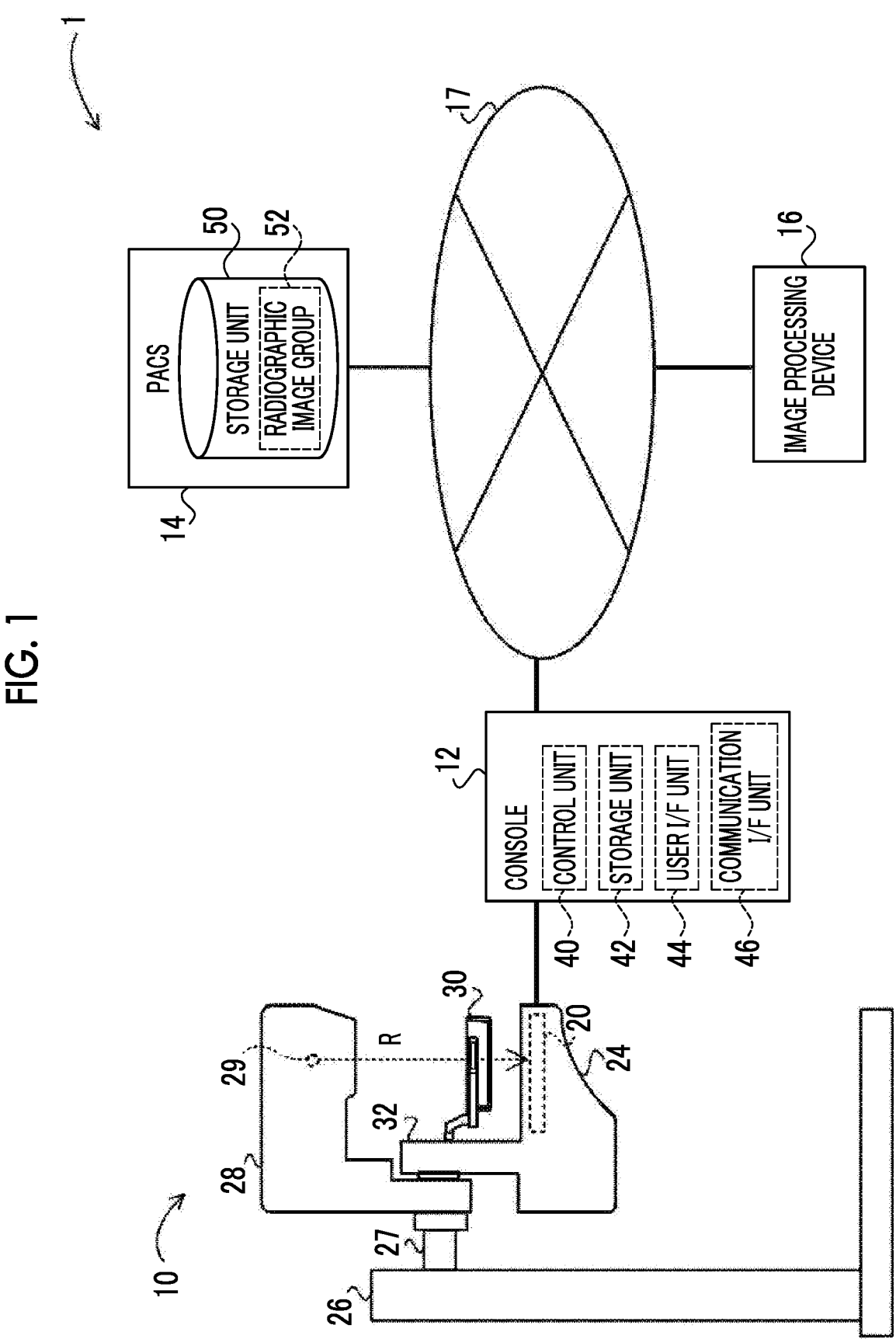
FIG. 1 is a schematic diagram illustrating an example of an overall configuration of a radiography system according to an embodiment.

First, an example of an overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10, a console 12, a picture archiving and communication system (PACS) 14, and an image processing device 16. The console 12, the PACS 14, and the image processing device 16 are connected by wired communication or wireless communication through a network 17.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from a left side of a subject.

The mammography apparatus 10 according to this embodiment is an apparatus that is operated under the control of the console 12 and that irradiates a breast of a subject as an object with radiation R (for example, X-rays) emitted from a radiation source 29 to capture a radiographic image of the breast. Further, the mammography apparatus 10 according to this embodiment has a function of performing normal imaging that captures images at an irradiation position where the radiation source 29 is disposed along a normal direction to a detection surface 20A of a radiation detector 20 and so-called tomosynthesis imaging (will be described in detail below) that captures images while moving the radiation source 29 to each of a plurality of irradiation positions.

As illustrated in FIG. 1, the mammography apparatus 10 comprises an imaging table 24, a base 26, an arm portion 28, and a compression unit 32.

Figure 2:
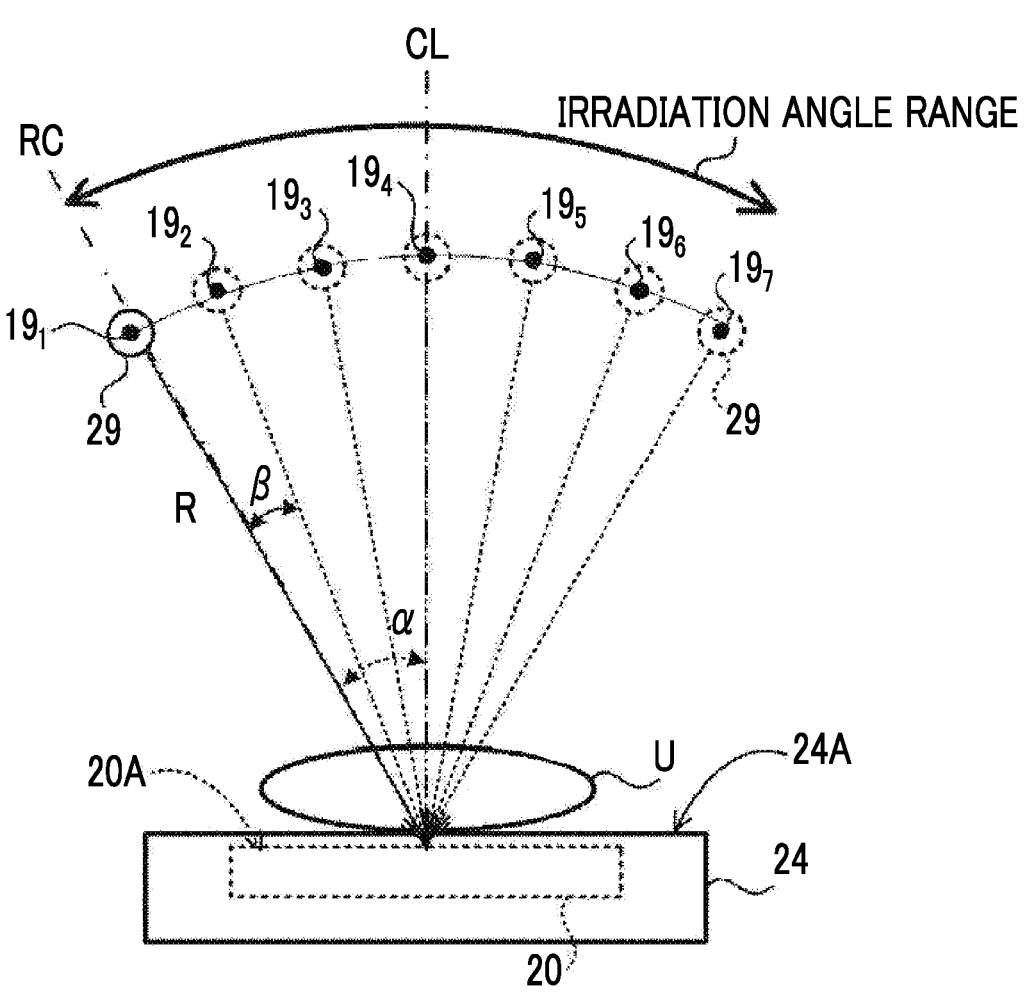
FIG. 2 is a diagram illustrating an example of tomosynthesis imaging.

The radiation detector 20 is provided in the imaging table 24. As illustrated in FIG. 2, in the mammography apparatus 10 according to this embodiment, in a case in which imaging is performed, the breast U of the subject is positioned on an imaging surface 24A of the imaging table 24 by a user.

The radiation detector 20 detects the radiation R transmitted through the breast U which is the object. Specifically, the radiation detector 20 detects the radiation R that has entered the breast U of the subject and the imaging table 24 and that has reached the detection surface 20A of the radiation detector 20, generates a radiographic image on the basis of the detected radiation R, and outputs image data indicating the generated radiographic image. In the following description, in some cases, a series of operations of emitting the radiation R from the radiation source 29 and generating a radiographic image using the radiation detector 20 is referred to as "imaging". The type of the radiation detector 20 according to this embodiment is not particularly limited. For example, the radiation detector 20 may be an indirect-conversion-type radiation detector that converts the radiation R into light and converts the converted light into charge or may be a direct-conversion-type radiation detector that directly converts the radiation R into charge.

A compression plate 30 used for compressing the breast during imaging is attached to the compression unit 32 provided on the imaging table 24 and is moved in a direction (hereinafter, referred to as an "up-down direction") toward or away from the imaging table 24 by a compression plate driving unit (not illustrated) that is provided in the compression unit 32. The compression plate 30 is moved in the up-down direction to compress the breast of the subject between the imaging table 24 and the compression plate 30.

The arm portion 28 can be rotated with respect to the base 26 by a shaft portion 27. The shaft portion 27 is fixed to the base 26, and the shaft portion 27 and the arm portion 28 are rotated integrally. Gears are provided in each of the shaft portion 27 and the compression unit 32 of the imaging table 24. The gears can be switched between an engaged state and a non-engaged state to switch between a state in which the compression unit 32 of the imaging table 24 and the shaft portion 27 are connected and rotated integrally and a state in which the shaft portion 27 is separated from the imaging table 24 and runs idle. In addition, components for switching between the transmission and non-transmission of power of the shaft portion 27 are not limited to the gears, and various mechanical elements may be used. Each of the arm portion 28 and the imaging table 24 can be relatively rotated with respect to the base 26, using the shaft portion 27 as a rotation axis.

In a case in which the tomosynthesis imaging is performed in the mammography apparatus 10, the radiation source 29 is sequentially moved to each of a plurality of irradiation positions having different irradiation angles by the rotation of the arm portion 28. The radiation source 29 includes a radiation tube (not illustrated) that generates the radiation R, and the radiation tube is moved to each of the plurality of irradiation positions according to the movement of the radiation source 29. FIG. 2 is a diagram illustrating an example of the tomosynthesis imaging. In addition, the compression plate 38 is not illustrated in FIG. 2. In this embodiment, as illustrated in FIG. 2, the radiation source 29 is moved to irradiation positions $19_t$ (t=1, 2, . . . ; the maximum value is 7 in FIG. 2) having different irradiation angles which are arranged at an interval of a predetermined angle β, that is, positions where the radiation R is emitted to the detection surface 20A of the radiation detector 20 at different angles. At each of the irradiation positions $19_t$, the radiation source 29 emits the radiation R to the breast U in response to an instruction from the console 12, and the radiation detector 20 captures a radiographic image. In the radiography system 1, in a case in which the tomosynthesis imaging that moves the radiation source 29 to each of the irradiation positions $19_t$ and captures radiographic images at each of the irradiation positions $19_t$ is performed, seven radiographic images are obtained in the example illustrated in FIG. 2. In addition, in the following description, in the tomosynthesis imaging, in a case in which the radiographic image captured at each irradiation position 19 is distinguished from other radiographic images, it is referred to as a "projection image", and a plurality of projection images captured by one tomosynthesis imaging operation are referred to as "a series of a plurality of projection images". Further, in a case in which radiographic images, such as a projection image, a tomographic image which will be described below, and a synthesized two-dimensional image, are generically referred to regardless of the type, they are simply referred to as "radiographic images". Further, in the following description, for the image corresponding to the irradiation position $19_t$, such as the projection image captured at each irradiation position $19_t$, the reference letter "t" indicating the irradiation position $19_t$ is given to the reference numeral indicating each image.

In addition, as illustrated in FIG. 2, the irradiation angle of the radiation R means an angle α formed between a normal line CL to the detection surface 20A of the radiation detector 20 and a radiation axis RC. The radiation axis RC means an axis that connects a focus of the radiation source 29 at each irradiation position 19 and a preset position such as a center of the detection surface 20A. Further, here, it is assumed that the detection surface 20A of the radiation detector 20 is substantially parallel to the imaging surface 24A.

Moreover, in a case in which the mammography apparatus 10 performs the normal imaging, the radiation source 29 remains at the irradiation position 19$_t$ (the irradiation position 19$_t$ along the normal direction; the irradiation position 19$_4$ in FIG. 2) where the irradiation angle α is 0 degrees. The radiation source 29 emits the radiation R in response to an instruction from the console 12, and the radiation detector 20 captures a radiographic image.

The mammography apparatus 10 and the console 12 are connected by wired communication or wireless communication. The radiographic image captured by the radiation detector 20 in the mammography apparatus 10 is output to the console 12 by wired communication or wireless communication through a communication interface (I/F) unit (not illustrated).

As illustrated in FIG. 1, the console 12 according to this embodiment comprises a control unit 40, a storage unit 42, a user I/F unit 44, and a communication I/F unit 46.

As described above, the control unit 40 of the console 12 has a function of controlling the capture of the radiographic image of the breast by the mammography apparatus 10. An example of the control unit 40 is a computer system comprising a central processing unit (CPU), a read only memory (ROM), and a random access memory (RAM).

The storage unit 42 has a function of storing, for example, information related to the acquisition of a radiographic image or the radiographic image acquired from the mammography apparatus 10. The storage unit 42 is a non-volatile storage unit and is, for example, a hard disk drive (HDD) or a solid state drive (SSD).

The user I/F unit 44 includes input devices, such as various buttons and switches operated by a user, such as a radiology technician, regarding the capture of a radiographic image, and display devices, such as lamps and displays, that display information related to imaging and the radiographic images obtained by imaging.

The communication I/F unit 46 transmits and receives various kinds of data, such as information related to the capture of radiographic images and the radiographic images, to and from the mammography apparatus 10 using wired communication or wireless communication. In addition, the communication I/F unit 46 transmits and receives various kinds of data, such as radiographic images, to and from the PACS 14 and the image processing device 16 through the network 17 using wired communication or wireless communication.

Further, as illustrated in FIG. 1, the PACS 14 according to this embodiment comprises a storage unit 50 that stores a radiographic image group 52 and a communication I/F unit (not illustrated). The radiographic image group 52 includes, for example, the radiographic image captured by the mammography apparatus 10 acquired from the console 12 through the communication I/F unit (not illustrated).

The image processing device 16 has a function of supporting a doctor's diagnosis by performing determination regarding the diagnosis of a lesion in a case in which the doctor or the like (hereinafter, simply referred to as a "doctor") makes a diagnosis on the lesion of the breast using radiographic images.

Figure 3:
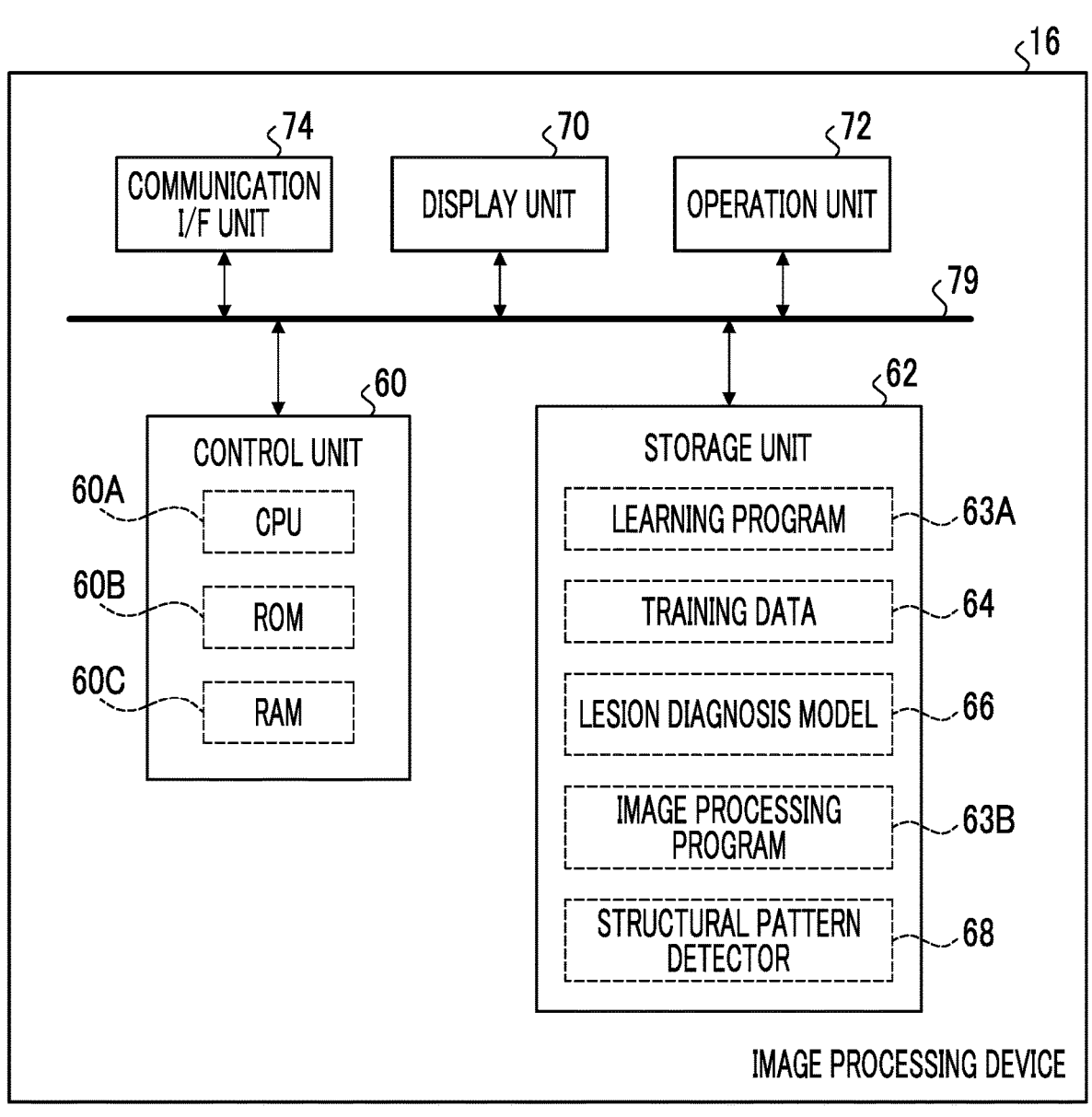
FIG. 3 is a block diagram illustrating an example of a configuration of an image processing device according to the embodiment.

FIG. 3 is a block diagram illustrating an example of the configuration of the image processing device 16 according to this embodiment. As illustrated in FIG. 3, the image processing device 16 according to this embodiment comprises a control unit 60, a storage unit 62, a display unit 70, an operation unit 72, and a communication I/F unit 74. The control unit 60, the storage unit 62, the display unit 70, the operation unit 72, and the communication I/F unit 74 are connected to each other through a bus 79, such as a system bus or a control bus, such that they can transmit and receive various kinds of information.

The control unit 60 controls the overall operation of the image processing device 16. The control unit 60 comprises a CPU 60A, a ROM 60B, and a RAM 60C. Various programs and the like used by the CPU 60A for control are stored in the ROM 60B in advance. The RAM 60C temporarily stores various kinds of data.

The storage unit 62 is a non-volatile storage unit and is, for example, an HDD or an SSD. The storage unit 62 stores various kinds of information such as a learning program 63A, an image processing program 63B, training data 64, a lesion diagnosis model 66, and a structural pattern detector 68, all of which will be described in detail below.

The display unit 70 displays radiographic images or various kinds of information. The display unit 70 is not particularly limited, and various displays and the like may be used. In addition, the operation unit 72 is used by the user to input instructions for the diagnosis of the lesion of the breast using a radiographic image by a doctor, various kinds of information, or the like. The operation unit 72 is not particularly limited. Examples of the operation unit 72 include various switches, a touch panel, a touch pen, and a mouse. In addition, the display unit 70 and the operation unit 72 may be integrated into a touch panel display.

The communication I/F unit 74 transmits and receives various kinds of information to and from the console 12 and the PACS 14 through the network 17 using wireless communication or wired communication.

Figure 4:
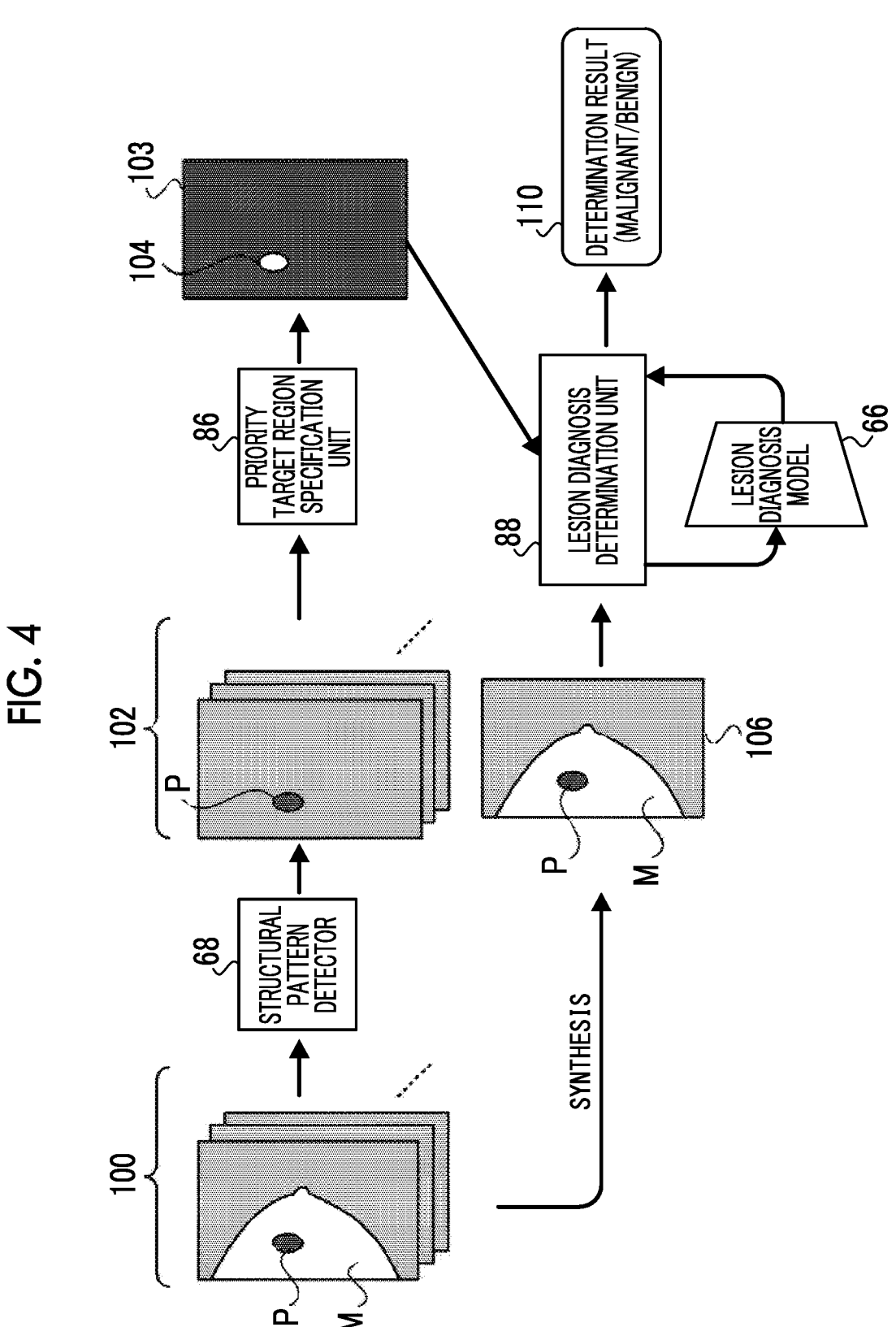
FIG. 4 is a schematic diagram illustrating an outline of a flow of determination regarding a diagnosis of a lesion in the image processing device according to the embodiment.

A function of performing the determination regarding the diagnosis of the lesion to support the doctor's diagnosis in the image processing device 16 according to this embodiment will be described. First, the outline of the determination regarding the diagnosis of the lesion in the image processing device 16 according to the embodiment will be described. FIG. 4 is a schematic diagram illustrating the outline of the flow of the determination regarding the diagnosis of the lesion in the image processing device 16 according to this embodiment.

The image processing device 16 according to this embodiment detects a specific structural pattern P indicating a lesion candidate structure of a breast M in each of a plurality of tomographic images 100. In a case in which the breast to be imaged includes a lesion, at least some of a plurality of tomographic images 100 obtained from a series of a plurality of projection images obtained by the tomosynthesis imaging include the specific structural pattern P indicating the lesion candidate structure. The image processing device 16 detects the specific structural pattern indicating the lesion candidate structure from each of the plurality of tomographic images 100 using the structural pattern detector 68.

For example, in this embodiment, a detector using a known computer-aided diagnosis (CAD) algorithm is used as the structural pattern detector 68. In the CAD algorithm, a probability (likelihood) indicating that a pixel in the tomographic image 100 will be the specific structural pattern P is derived, and a pixel having a probability equal to or greater than a predetermined threshold value is detected as the specific structural pattern P.

Further, the detection result of the structural pattern detector 68 according to this embodiment is output as a mask image 102 in which the position of the specific structural pattern P is shown. In other words, the mask image 102 obtained as the detection result of the structural pattern detector 68 is an image showing the position of the specific structural pattern P in each tomographic image 100. For example, the mask image 102 according to this embodiment is a binary image in which the specific structural pattern P is represented by "1" and the others are represented by "0". In addition, the mask image 102 is obtained for each of the plurality of tomographic images 100. That is, the same number of mask images 102 as the plurality of tomographic images 100 is obtained.

Further, the image processing device 16 synthesizes the plurality of tomographic images 100 to generate a synthesized two-dimensional image 106. The synthesized two-dimensional image 106 includes the breast M and the specific structural pattern P.

Furthermore, the image processing device 16 specifies a priority target region 104, in which the specific structural pattern P is present, in the synthesized two-dimensional image 106 from the mask image 102 using a priority target region specification unit 86. The priority target region 104 is a region, in which the specific structural pattern P is present, in the synthesized two-dimensional image 106, and the determination regarding the diagnosis of the lesion is focused on the priority target region 104. The priority target region specification unit 86 outputs a mask image 103 indicating the priority target region 104 in which the specific structural pattern P is present as a specification result.

Then, in the image processing device 16, a lesion diagnosis determination unit 88 performs the determination regarding the diagnosis of the lesion on the basis of the synthesized two-dimensional image 106 and the priority target region 104 specified by the priority target region specification unit 86, using a lesion diagnosis model 66, and obtains a determination result 110 indicating whether the lesion is malignant or benign.

Figure 5:
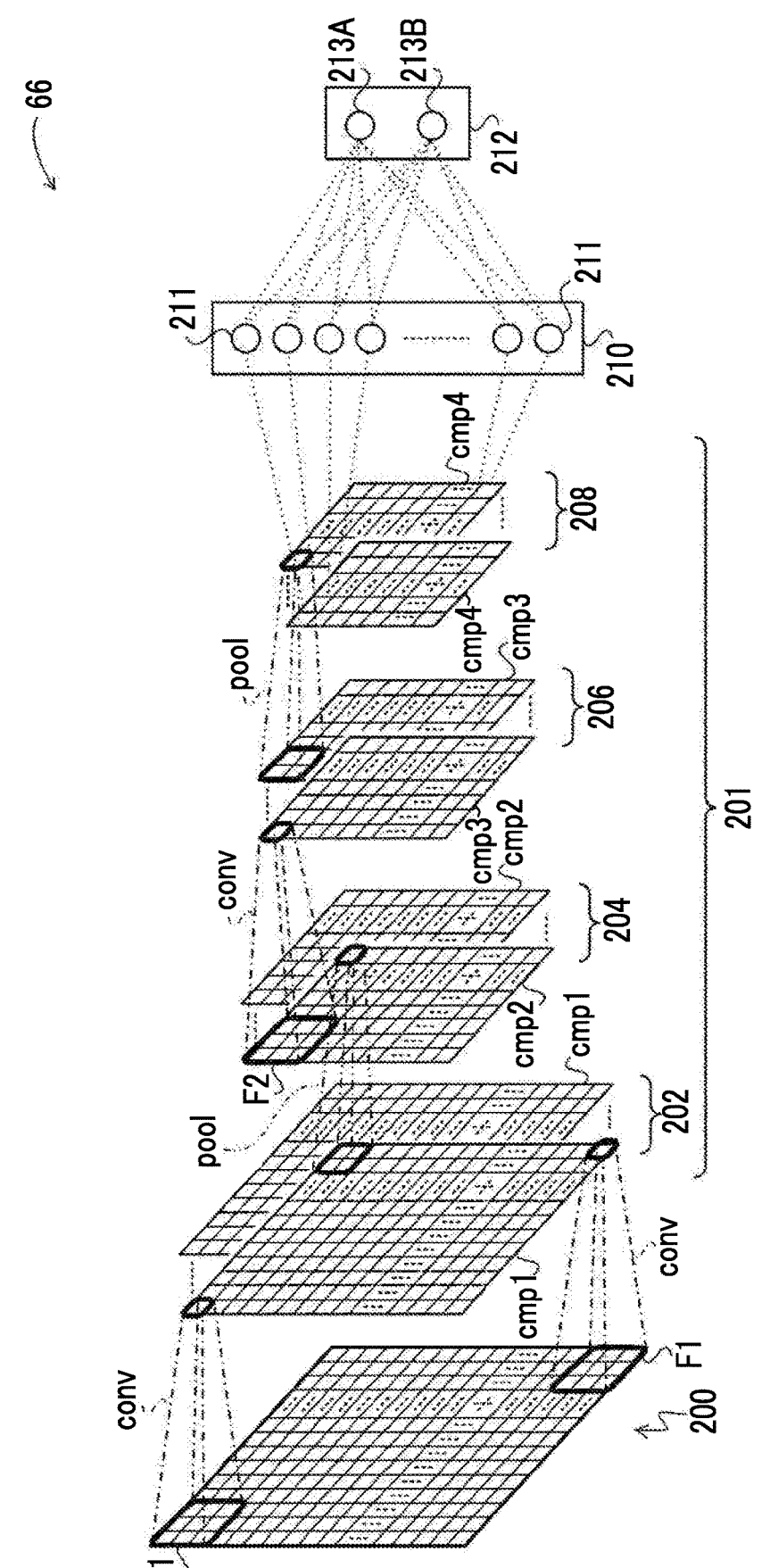
FIG. 5 is a diagram illustrating an example of a lesion diagnosis model.

For example, in this embodiment, a convolutional neural network (CNN) that has been subjected to machine learning by deep learning using the training data 64 is used as the lesion diagnosis model 66. FIG. 5 illustrates an example of the lesion diagnosis model 66 according to this embodiment.

The lesion diagnosis model 66 illustrated in FIG. 5 comprises an input layer 200, a middle layer 201, a flat layer 210, and an output layer 212. An image (the synthesized two-dimensional image 106 in this embodiment) to be processed is input to the input layer 200. The input layer 200 transmits information of each pixel (every pixel) of the input image to be processed to the middle layer 201 without any change. For example, in a case in which the image to be processed has a size of 28 pixels×28 pixels and is grayscale data, the size of the data transmitted from the input layer 200 to the middle layer 201 is 28×28×1=784.

The middle layer 201 includes convolution layers 202 and 206 that perform a convolution process (conv) and pooling layers 204 and 208 that perform a pooling process (pool).

Figure 6:
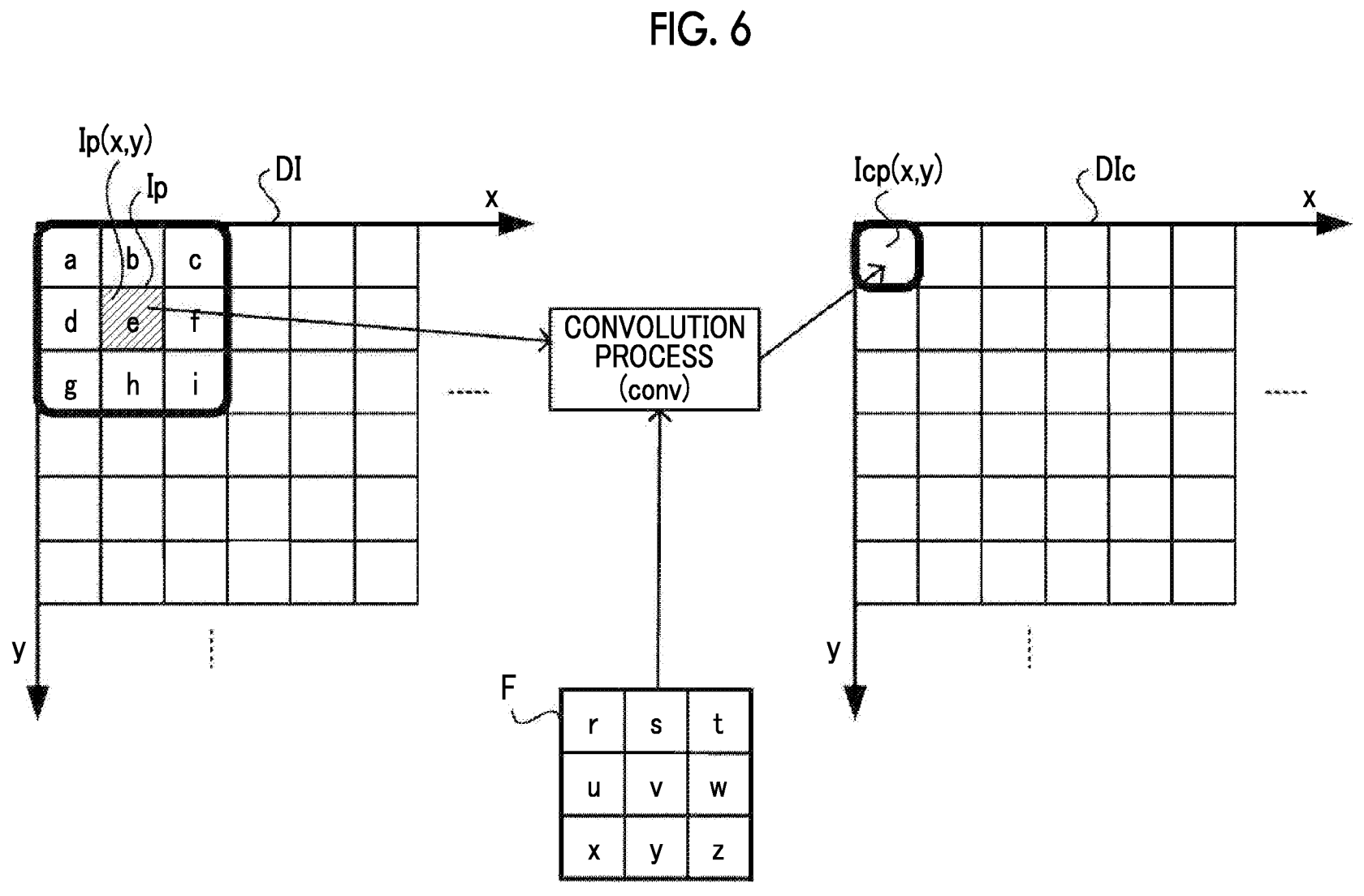

The convolution process performed by the convolution layers 202 and 206 will be described with reference to FIG. 6. As illustrated in FIG. 6, in the convolution process, in a case in which a pixel value Ip(x, y) of a pixel of interest Ip in input data DI is "e", the pixel values of the surrounding adjacent pixels are "a" to "d" and "f" to "i", and coefficients of a 3×3 filter F are "r" to "z", a pixel value Icp(x, y) of a pixel Icp in output data DIc, which is the result of a convolution operation for the pixel of interest Ip, is obtained according to, for example, the following Expression (1). In addition, the coefficient of the filter F corresponds to a weight indicating the strength of the connection between nodes of the previous and next layers.

$$Icp(x,y)=a{\times}z+b{\times}y+c{\times}x+d{\times}w+e{\times}v+f{\times}u+g{\times}t+h{\times}s+i{\times}r \tag{1}$$

In the convolution process, the above-mentioned convolution operation is performed for each pixel, and the pixel value Icp(x, y) corresponding to each pixel of interest Ip is output. In this way, the output data DIc having the pixel values Icp(x, y) that are two-dimensionally arranged is output. One output data item DIc is output for one filter F. In a case in which a plurality of filters F of different types are used, the output data DIc is output for each filter F. The filter F means a neuron (node) of the convolution layer, and the features that can be extracted are determined for each filter F. Therefore, the number of features that can be extracted from one input data item DI in the convolution layer is the number of filters F.

Further, in the pooling layers 204 and 208, a pooling process that reduces the original image while maintaining the features is performed. In other words, in the pooling layers 204 and 208, a pooling process that selects a local representative value and reduces the resolution of the input image to reduce the size of the image is performed. For example, in a case in which the pooling process of selecting a representative value from a block of 2×2 pixels is performed with a stride of "1", that is, by shifting the pixel one by one, a reduced image obtained by reducing the size of the input image by half is output.

In this embodiment, as illustrated in FIG. 5, the convolution layers 202 and 206 and the pooling layers 204 and 208 are disposed in the order of the convolution layer 202, the pooling layer 204, the convolution layer 206, and the pooling layer 208 from the side closest to the input layer 200.

As illustrated in FIG. 5, the convolution layer 202 applies a 3×3 filter F1 to the input (transmitted) image to perform the above-mentioned convolution operation and outputs an image feature map cmp1 from which the features of the input image have been extracted and in which pixel values are two-dimensionally arranged. As described above, the number of image feature maps cmp1 corresponds to the type of filter F1.

The pooling layer 204 performs the pooling process of selecting a representative value from a block of 2×2 pixels for the image feature map cmp1 to reduce the size of the image feature map cmp1 to ¼ (the vertical and horizontal sizes are reduced to ½) and outputs a plurality of image feature maps cmp2.

Similarly to the convolution layer 202, the convolution layer 206 applies a 3×3 filter F2 to perform the above-mentioned convolution operation and outputs a plurality of image feature maps cmp3 from which the features of the input image feature maps cmp2 have been extracted and in which pixel values are two-dimensionally arranged.

Similarly to the pooling layer 204, the pooling layer 208 performs the pooling process of selecting a representative value from a block of 2×2 pixels for the image feature map cmp3 to reduce the size of the image feature map cmp3 to ¼ (the vertical and horizontal sizes are reduced to ½) and outputs a plurality of image feature maps cmp4.

The flat layer 210 after the middle layer 201 rearranges data in a state in which the numerical value of the data is maintained as the image feature map cmp4. For example, as illustrated in FIG. 5, the flat layer 210 rearranges three-dimensional data indicated by a plurality of image feature maps cmp4 as one-dimensional data. As illustrated in FIG. 5, the value of each node 211 included in the flat layer 210 corresponds to the pixel value of each pixel of the plurality of image feature maps cmp4.

The output layer 212 is a fully connected layer to which all of the nodes 211 are connected and includes a node 213A corresponding to the determination that the lesion is malignant and a node 213B corresponding to the determination that the lesion is benign. The output layer 212 outputs a probability corresponding to the determination that the lesion is malignant, which corresponds to the node 213A, and a probability corresponding to the determination that the lesion is benign, which corresponds to the node 213B, using a softmax function which is an example of an activation function.

Further, the lesion diagnosis model 66 outputs a determination result indicating that the lesion is malignant in a case in which the probability of the node 213A is equal to or higher than the probability of the node 213B in the output layer 212. On the other hand, the lesion diagnosis model 66 outputs a determination result indicating that the lesion is benign in a case in which the probability of the node 213A is lower than the probability of the node 213B in the output layer 212. In addition, the lesion diagnosis model 66 may output information indicating the probability of the nodes 213A and 213B as the determination result instead of outputting the "malignant" and "benign" labels as the determination result.

Figure 7:
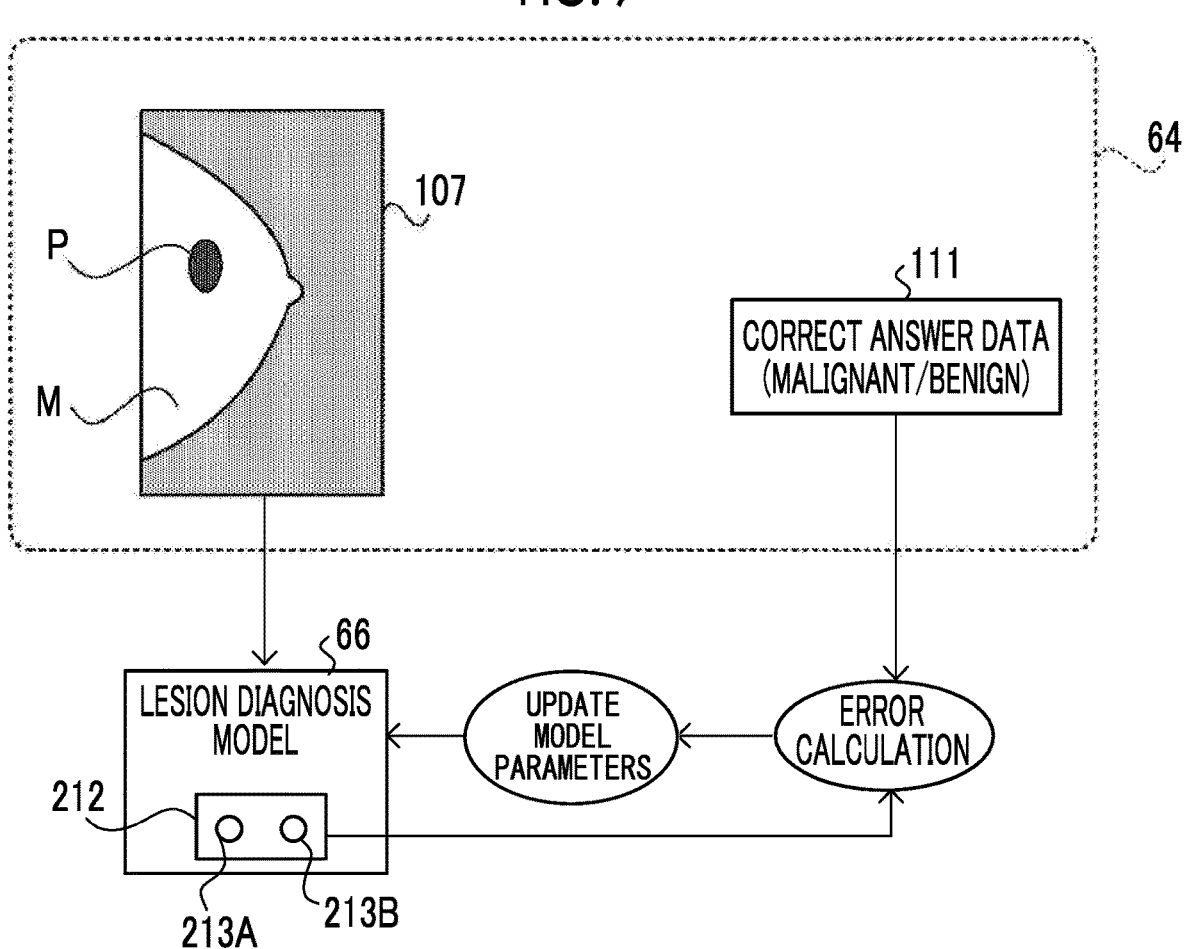
FIG. 7 is a diagram illustrating an example of a learning phase in which the image processing device trains the lesion diagnosis model via machine learning.

The image processing device 16 according to this embodiment performs machine learning on a machine learning model using the training data 64 to generate the lesion diagnosis model 66 according to this embodiment. An example of a learning phase in which the image processing device 16 performs machine learning on the lesion diagnosis model 66 will be described with reference to FIG. 7.

The training data 64 is composed of a set of a synthesized two-dimensional image 107 and correct answer data 111. The correct answer data 111 is information indicating whether the lesion indicated by the specific structural pattern P included in the synthesized two-dimensional image 107 is malignant or benign. In this embodiment, machine learning is performed on the lesion diagnosis model 66 using a back propagation method.

In the learning phase, the synthesized two-dimensional image 107 of the training data 64 is input to the lesion diagnosis model 66. In addition, in this embodiment, the synthesized two-dimensional image 107 may be divided into a plurality of batches (images), and the divided batches may be sequentially input to the lesion diagnosis model 66 for training.

Further, the training data 64 used for training the lesion diagnosis model 66 is not limited to this embodiment. For example, a synthesized two-dimensional image 107 including the specific structural pattern P for a benign lesion and a synthesized two-dimensional image 107 including the specific structural pattern P for a malignant lesion may be used. In addition, for example, a synthesized two-dimensional image 107 including the specific structural pattern P for a benign lesion, a synthesized two-dimensional image 107 including a structural pattern of a normal structure (tissue) similar to a lesion, and a synthesized two-dimensional image 107 including the specific structural pattern P for a malignant lesion may be used as the training data 64.

The lesion diagnosis model 66 outputs the determination result corresponding to the specific structural pattern P included in the synthesized two-dimensional image 107, specifically, the values of the nodes 213A and 213B included in the output layer 212 of the lesion diagnosis model 66.

Furthermore, in a case in which the correct answer data 111 for the synthesized two-dimensional image 107 input to the lesion diagnosis model 66 is "malignant", the value of the node 213A needs to be "1", and the value of the node 213B needs to be "0". Further, in a case in which the correct answer data 111 for the synthesized two-dimensional image 107 input to the lesion diagnosis model 66 is "benign", the value of the node 213A needs to be "0", and the value of the node 213B needs to be "1".

Therefore, the difference (error) between the values of the nodes 213A and 213B output from the lesion diagnosis model 66 and the values to be taken by the nodes 213A and 213B corresponding to the correct answer data 111 is calculated. Then, an update setting of a weight for each neuron is performed according to the error using the back propagation method such that the error is reduced from the output layer 212 to the input layer 200, and the lesion diagnosis model 66 is updated according to the update setting.

In the learning phase, a series of processes of the input of the synthesized two-dimensional image 107 of the training data 64 to the lesion diagnosis model 66, the output of each of the values of the nodes 213A and 213B included in the output layer 212 from the lesion diagnosis model 66, the calculation of the error based on each of the values of the nodes 213A and 213B and the correct answer data 111, the update setting of the weights, and the update of the lesion diagnosis model 66 is repeatedly performed.

Figure 8:
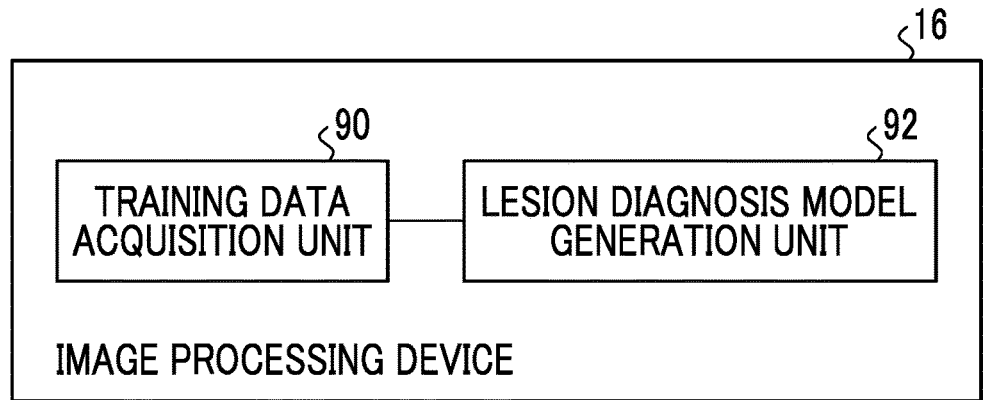
FIG. 8 is a functional block diagram illustrating an example of a configuration related to a function of generating the lesion diagnosis model in the image processing device according to the embodiment.

FIG. 8 is a functional block diagram illustrating an example of a configuration related to a function of generating the lesion diagnosis model 66 in the image processing device 16 according to this embodiment. As illustrated in FIG. 8, the image processing device 16 comprises a training data acquisition unit 90 and a lesion diagnosis model generation unit 92. For example, in the image processing device 16 according to this embodiment, the CPU 60A of the control unit 60 executes the learning program 63A stored in the storage unit 62 to function as the training data acquisition unit 90 and the lesion diagnosis model generation unit 92.

The training data acquisition unit 90 has a function of acquiring the training data 64 from the storage unit 62. In addition, one training data item 64 is illustrated in FIG. 3. However, in practice, a sufficient amount of training data 64 to train the lesion diagnosis model 66 is stored in the storage unit 62. Further, the correct answer data 111, that is, whether the specific structural pattern P included in the synthesized two-dimensional image 107 is malignant or benign, is set on the basis of the determination of an expert, such as a doctor, or the result of biopsy or cytodiagnosis. The training data acquisition unit 90 outputs the acquired training data 64 to the lesion diagnosis model generation unit 92.

The lesion diagnosis model generation unit 92 has a function of performing machine learning on the machine learning model using the training data 64 as described above to generate the lesion diagnosis model 66 that receives the synthesized two-dimensional image 106 as an input and that outputs the result of the determination of whether the specific structural pattern P included in the synthesized two-dimensional image 106 is malignant or benign. The lesion diagnosis model generation unit 92 stores the generated lesion diagnosis model 66 in the storage unit 62.

Next, the operation of the image processing device 16 according to this embodiment in the learning phase will be described with reference to FIG. 9. The CPU 60A executes the learning program 63A stored in the storage unit 62 such that a learning process illustrated in FIG. 9 is performed.

Figure 9:
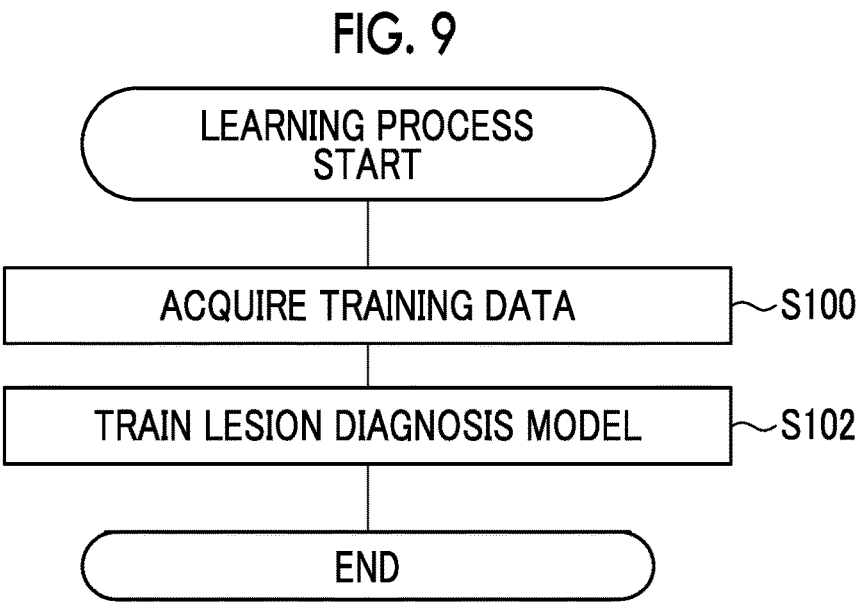
FIG. 9 is a flowchart illustrating an example of a flow of a learning process by the image processing device according to the embodiment.

In Step S100 of FIG. 9, the training data acquisition unit 90 acquires the training data 64 from the storage unit 62 as described above.

Then, in Step S102, the lesion diagnosis model generation unit 92 trains the lesion diagnosis model 66 using the training data 64 acquired in Step S100. As described above, the lesion diagnosis model generation unit 92 repeatedly performs a series of processes of the input of the synthesized two-dimensional image 107 included in the training data 64 to the lesion diagnosis model 66, the output of each of the values of the nodes 213A and 213B included in the output layer 212 of the lesion diagnosis model 66, the calculation of the error between each of the values of the nodes 213A and 213B and the correct answer data 111, the update setting of the weights, and the update of the lesion diagnosis model 66 to train the lesion diagnosis model 66. The lesion diagnosis model generation unit 92 stores the trained lesion diagnosis model 66 in the storage unit 62. In a case in which the process in Step S102 ends, the learning process illustrated in FIG. 9 ends.

The lesion diagnosis model 66 generated by the learning phase in the image processing device 16 as described above is used as the operation phase as described above in a case in which the determination regarding the diagnosis of the lesion in the image processing device 16 is performed. The function of performing the determination of the diagnosis of the lesion in the image processing device 16 according to this embodiment will be described in detail with reference to FIG. 4 that has been described above.

Figure 10:
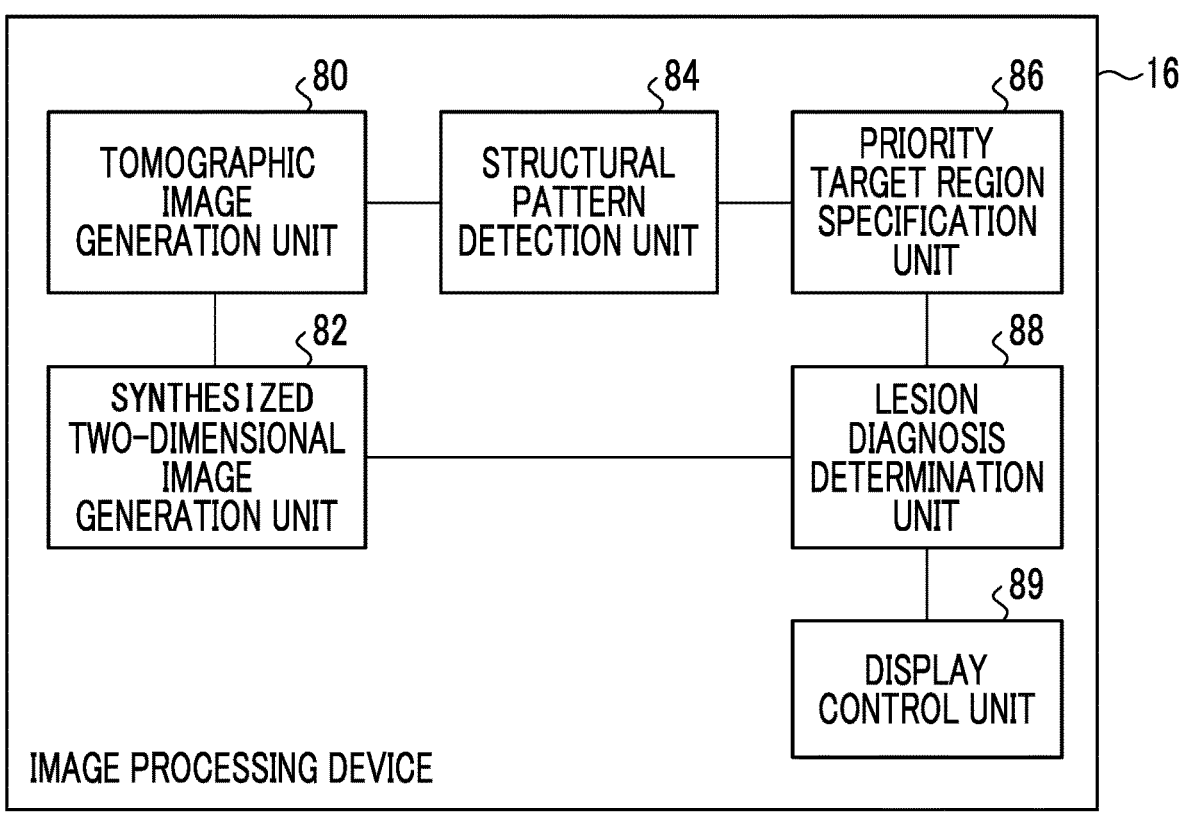
FIG. 10 is a functional block diagram illustrating an example of a configuration related to a function of performing the determination regarding the diagnosis of the lesion in the image processing device according to the embodiment.

FIG. 10 is a functional block diagram illustrating an example of a configuration related to a function of performing the determination regarding the diagnosis of the lesion in the image processing device 16. As illustrated in FIG. 10, the image processing device 16 comprises a tomographic image generation unit 80, a synthesized two-dimensional image generation unit 82, a structural pattern detection unit 84, a priority target region specification unit 86, a lesion diagnosis determination unit 88, and a display control unit 89. For example, in the image processing device 16 according to this embodiment, the CPU 60A of the control unit 60 executes the image processing program 63B stored in the storage unit 62 to function as the tomographic image generation unit 80, the synthesized two-dimensional image generation unit 82, the structural pattern detection unit 84, the priority target region specification unit 86, the lesion diagnosis determination unit 88, and the display control unit 89.

The tomographic image generation unit 80 has a function of generating a plurality of tomographic images from a series of a plurality of projection images. The tomographic image generation unit 80 acquires a desired series of a plurality of projection images from the console 12 of the mammography apparatus 10 or from the PACS 14 in response to an instruction to diagnose a lesion. Then, the tomographic image generation unit 80 generates a plurality of tomographic images 100 having different heights from the imaging surface 24A from the acquired series of the plurality of projection images. In addition, the method by which the tomographic image generation unit 80 generates the plurality of tomographic images 100 is not particularly limited. For example, the tomographic image generation unit 80 reconstructs a series of a plurality of projection images using a back projection method, such as a filter back projection (FBP) method or an iterative reconstruction method, to generate the plurality of tomographic images 100. The tomographic image generation unit 80 outputs the generated plurality of tomographic images 100 to the synthesized two-dimensional image generation unit 82 and to the structural pattern detection unit 84.

As described with reference to FIG. 4, the structural pattern detection unit 84 has a function of detecting the specific structural pattern P from each of the plurality of tomographic images 100 using the structural pattern detector 68. The structural pattern detection unit 84 according to this embodiment sequentially inputs the plurality of tomographic images 100 to the structural pattern detector 68 such that the structural pattern detector 68 outputs the mask image 102 indicating the position of the specific structural pattern P in each tomographic image 100.

As described with reference to FIG. 4, the priority target region specification unit 86 specifies the priority target region 104 which is a region in which the specific structural pattern P is present in the synthesized two-dimensional image 106 on the basis of a plurality of mask images 102. The mask image 102 is an image showing the position of the specific structural pattern P in each tomographic image 100. The tomographic images 100 have different heights of tomographic planes, that is, different distances from the radiation source 37R to the tomographic planes. Therefore, even in a case in which the same specific structural pattern P is present, for example, the position or size of the specific structural pattern P may differ depending on the tomographic image 100. Therefore, even in a case in which the same specific structural pattern P is present, for example, the position or size of the specific structural pattern P indicated by the mask image 102 may differ depending on the corresponding tomographic image 100. The priority target region specification unit 86 specifies the priority target region 104 which is a region in which the specific structural pattern P is present in the synthesized two-dimensional image 106 on the basis of the plurality of mask images 102.

In addition, the method by which the priority target region specification unit 86 specifies the priority target region 104 in the synthesized two-dimensional image 106 is not particularly limited. For example, the priority target region specification unit 86 synthesizes the plurality of mask images 102, using the same method by which the synthesized two-dimensional image generation unit 82 generates the synthesized two-dimensional image 106 from the plurality of tomographic images 100, to generate a synthesized mask image. Further, the priority target region specification unit 86 specifies a region including the specific structural pattern P in the generated synthesized mask image as the priority target region 104. The specification result of the priority target region specification unit 86 is output as the mask image 103 indicating the priority target region 104. In other words, the mask image 103 obtained as the specification result of the priority target region specification unit 86 is an image indicating the priority target region 104 in the synthesized two-dimensional image 106. The mask image 103 has the same size as the synthesized two-dimensional image 106. For example, the mask image 103 according to this embodiment is a binary image in which the priority target region 104 is represented by "1" and the other region is represented by "0". The priority target region specification unit 86 outputs the mask image 103 to the lesion diagnosis determination unit 88.

Meanwhile, the synthesized two-dimensional image generation unit 82 has a function of synthesizing the plurality of tomographic images 100 to generate the synthesized two-dimensional image 106. In addition, the method by which the synthesized two-dimensional image generation unit 82 generates the synthesized two-dimensional image 106 is not particularly limited, and the method disclosed in JP2014-128716A or U.S. Pat. No. 8,983,156B can be used. For example, the synthesized two-dimensional image generation unit 82 can synthesize the plurality of tomographic images 100 using an addition method, an averaging method, a maximum intensity projection method, a minimum intensity projection method, or the like to generate the synthesized two-dimensional image 106. The synthesized two-dimensional image generation unit 82 outputs the generated synthesized two-dimensional image 106 to the lesion diagnosis determination unit 88. In addition, the synthesized two-dimensional image generation unit 82 may generate the synthesized two-dimensional image 106 using the information of the plurality of mask images 102 which are the detection results of the structural pattern detector 68. Further, the process of specifying the priority target region 104 by the priority target region specification unit 86 may be incorporated into a reconstruction process in a case in which the synthesized two-dimensional image generation unit 82 reconstructs the plurality of tomographic images 100 to generate the synthesized two-dimensional image 106.

As described with reference to FIG. 4 and the like, the lesion diagnosis determination unit 88 has a function of determining whether the lesion is malignant or benign, using the lesion diagnosis model 66, in the diagnosis of the lesion of the breast. Further, the lesion diagnosis determination unit 88 according to this embodiment has a function of focusing the determination regarding the diagnosis of the lesion more on the priority target region 104 than on the other region in the synthesized two-dimensional image 106. In other words, the lesion diagnosis determination unit 88 has a function of performing the determination regarding the diagnosis of the lesion on the synthesized two-dimensional image 106 while focusing on the priority target region 104.

Figure 11:
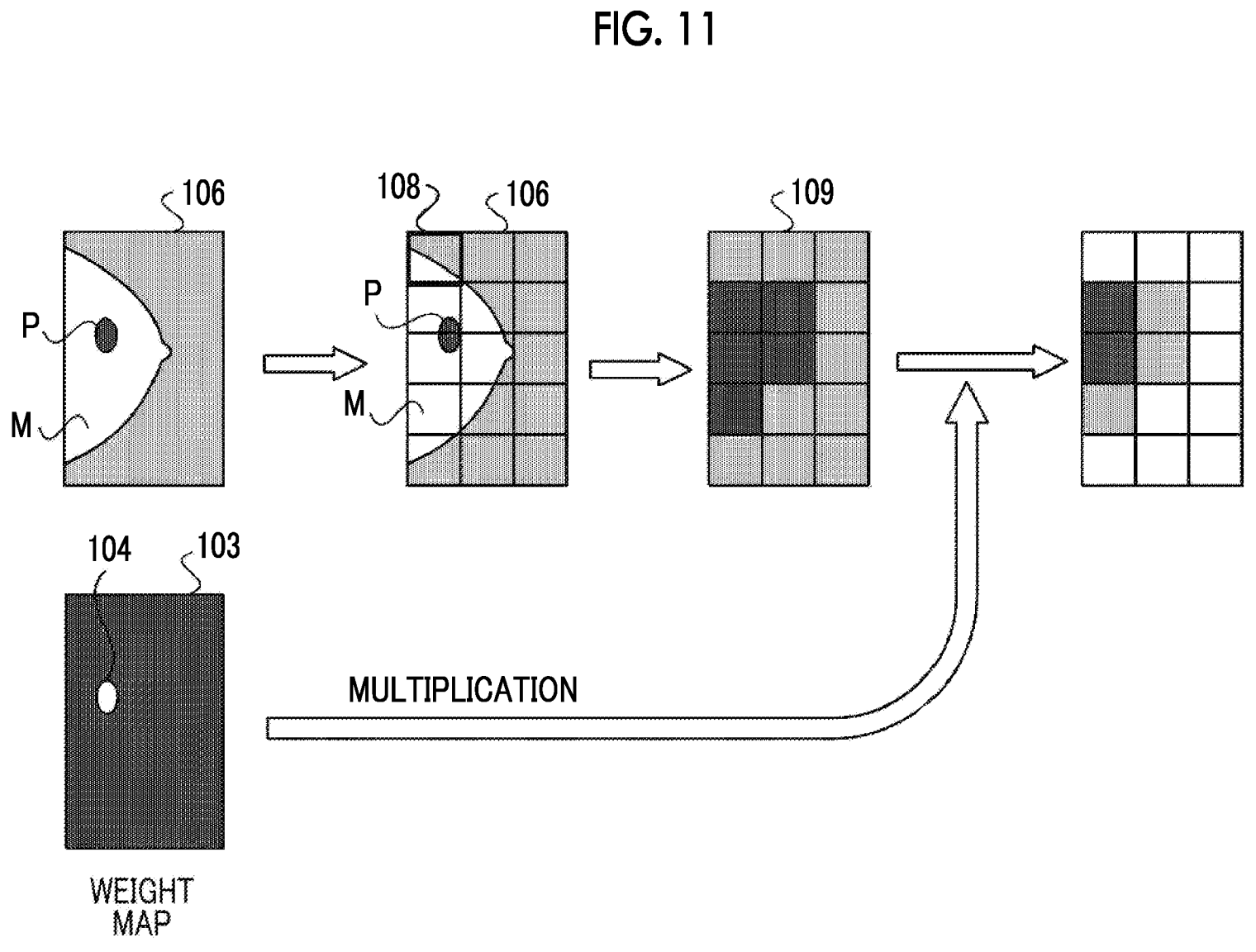

An example in which the lesion diagnosis determination unit 88 focuses the determination regarding the diagnosis of the lesion on the priority target region 104 will be described with reference to FIG. 11. The lesion diagnosis determination unit 88 performs the determination regarding the diagnosis of the lesion by setting a weight for the priority target region 104 to be larger than a weight for the other region in the synthesized two-dimensional image 106. Specifically, as illustrated in FIG. 11, the lesion diagnosis determination unit 88 divides the synthesized two-dimensional image 106 into a plurality of (15 in FIG. 11) regions 108 and inputs each region 108 to the lesion diagnosis model 66 such that the lesion diagnosis model 66 outputs the probability of the node 213A as the probability that the region 108 will be malignant for each region 108. Therefore, a likelihood map 109 indicating the probability of being malignant for the entire synthesized two-dimensional image 106 is generated. The lesion diagnosis determination unit 88 generates a weight map in which the weight for the priority target region 104 is larger than the weight for the other region on the basis of the mask image 103. The lesion diagnosis determination unit 88 performs the determination regarding the diagnosis of the lesion using the likelihood map and the weight map. For example, in a case in which a value obtained by multiplying the likelihood indicated by the likelihood map 109 by the weight of the weight map for each corresponding region or pixel is greater than a predetermined threshold value, the lesion diagnosis determination unit 88 determines that the region (pixel) is malignant. Further, the lesion diagnosis determination unit 88 determines that the lesion is benign in a case in which it is not malignant. The lesion diagnosis determination unit 88 outputs information indicating whether the lesion is malignant or benign as a determination result 110 to the display control unit 89.

The display control unit 89 has a function of performing control to display the information indicating the determination result 110 obtained by the lesion diagnosis determination unit 88 on the display unit 70.

Next, the operation of performing the determination regarding the diagnosis of the lesion in the image processing device 16 according to this embodiment will be described with reference to FIG. 12. The CPU 60A executes the image processing program 63B stored in the storage unit 62 such that a lesion diagnosis determination process illustrated in FIG. 12 is performed.

Figure 12:
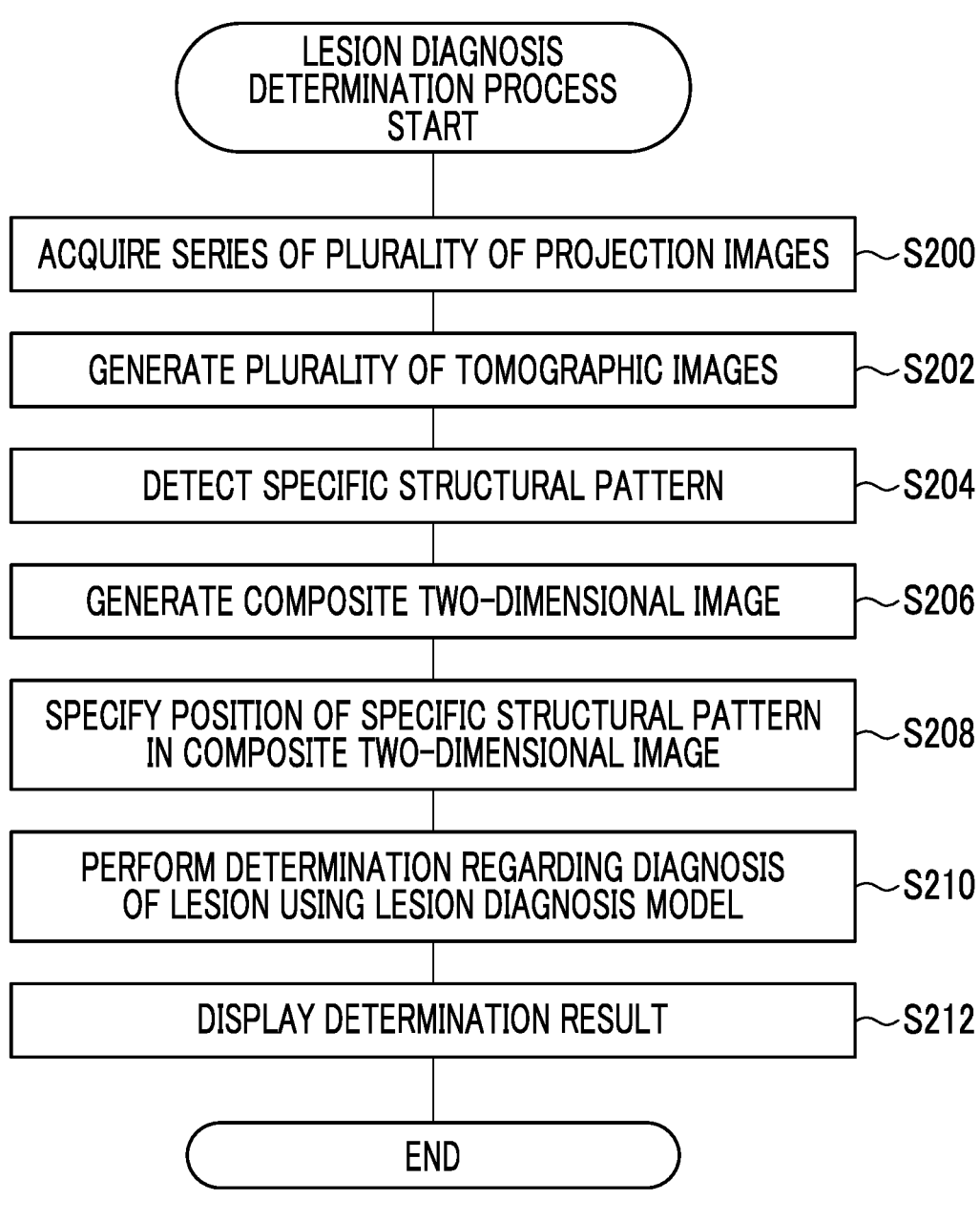
FIG. 12 is a flowchart illustrating an example of a flow of a lesion diagnosis determination process by the image processing device according to the embodiment.

In Step S200 of FIG. 12, the tomographic image generation unit 80 acquires a series of a plurality of projection images from the console 12 of the mammography apparatus 10 or from the PACS 14 as described above.

Then, in Step S202, the tomographic image generation unit 80 generates a plurality of tomographic images 100 from the series of the plurality of projection images acquired in Step S200.

Then, in Step S204, the structural pattern detection unit 84 detects the specific structural pattern P from each of the plurality of tomographic images 100 using the structural pattern detector 68 and obtains a plurality of mask images 102 as the detection results as described above.

Then, in Step S206, the synthesized two-dimensional image generation unit 82 generates the synthesized two-dimensional image 106 from the plurality of tomographic images 100 generated in Step S202 as described above.

Then, in Step S208, the priority target region specification unit 86 specifies the priority target region 104 which is a region corresponding to the position of the specific structural pattern P in the synthesized two-dimensional image 106 generated in Step S206, using the plurality of mask images 102, as described above. The priority target region specification unit 86 outputs the mask image 103 indicating the priority target region 104 as the specification result.

Then, in Step S210, the lesion diagnosis determination unit 88 performs the determination regarding the diagnosis of the lesion using the lesion diagnosis model 66 as described above. Specifically, the synthesized two-dimensional image 106 is input to the lesion diagnosis model 66, and the determination result output from the lesion diagnosis model 66 is acquired and used as the likelihood map 109. As described above, the lesion diagnosis model 66 focuses on the priority target region 104 using the likelihood map 109 and the mask image 103 indicating the priority target region 104 to perform the determination regarding the diagnosis of the lesion and outputs the determination result 110.

Figure 13:
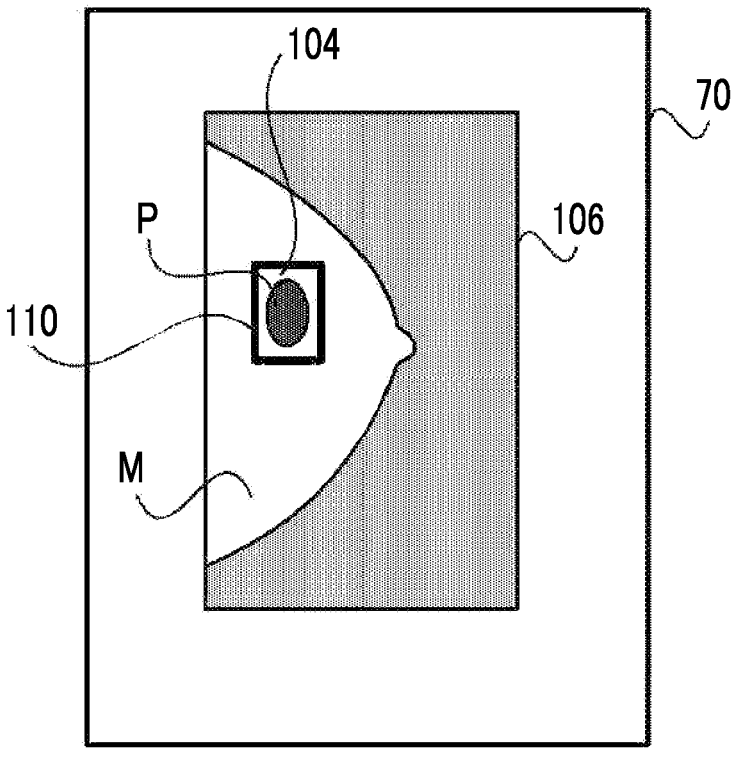
FIG. 13 is a diagram illustrating an example of a display aspect of a determination result.

Then, in Step S212, the display control unit 89 performs control to display the determination result 110 obtained by the determination regarding the diagnosis of the lesion in Step S210 on the display unit 70. In addition, the display aspect of displaying the determination result 110 on the display unit 70 is not particularly limited. FIG. 13 illustrates an example of the aspect in which the determination result 110 is displayed on the display unit 70 together with the synthesized two-dimensional image 106. In the example illustrated in FIG. 13, the determination result 110 is illustrated as a frame indicating the priority target region 104 including the specific structural pattern P in the synthesized two-dimensional image 106. The determination result 110 may be displayed by making the color of the frame, the type of a line indicating the frame, and the like differ depending on the determination result 110. As a specific example, in a case in which the determination result 110 is "malignant", the determination result 110 is displayed as a red line. In a case in which the determination result 110 is "benign", the determination result 110 is displayed as a blue line. Further, the present disclosure is not limited to the aspect illustrated in FIG. 13. For example, characters or symbols indicating the determination result 110 may be displayed on the display unit 70.

In addition, the aspects of, for example, the detection of the specific structural pattern P in the learning phase and the operation phase and the determination regarding the diagnosis of the lesion using the lesion diagnosis model 66 are examples, and various modification examples can be made. Hereinafter, some modification examples will be described.

MODIFICATION EXAMPLE 1

Modification Example of Operation Phase

Figure 14:
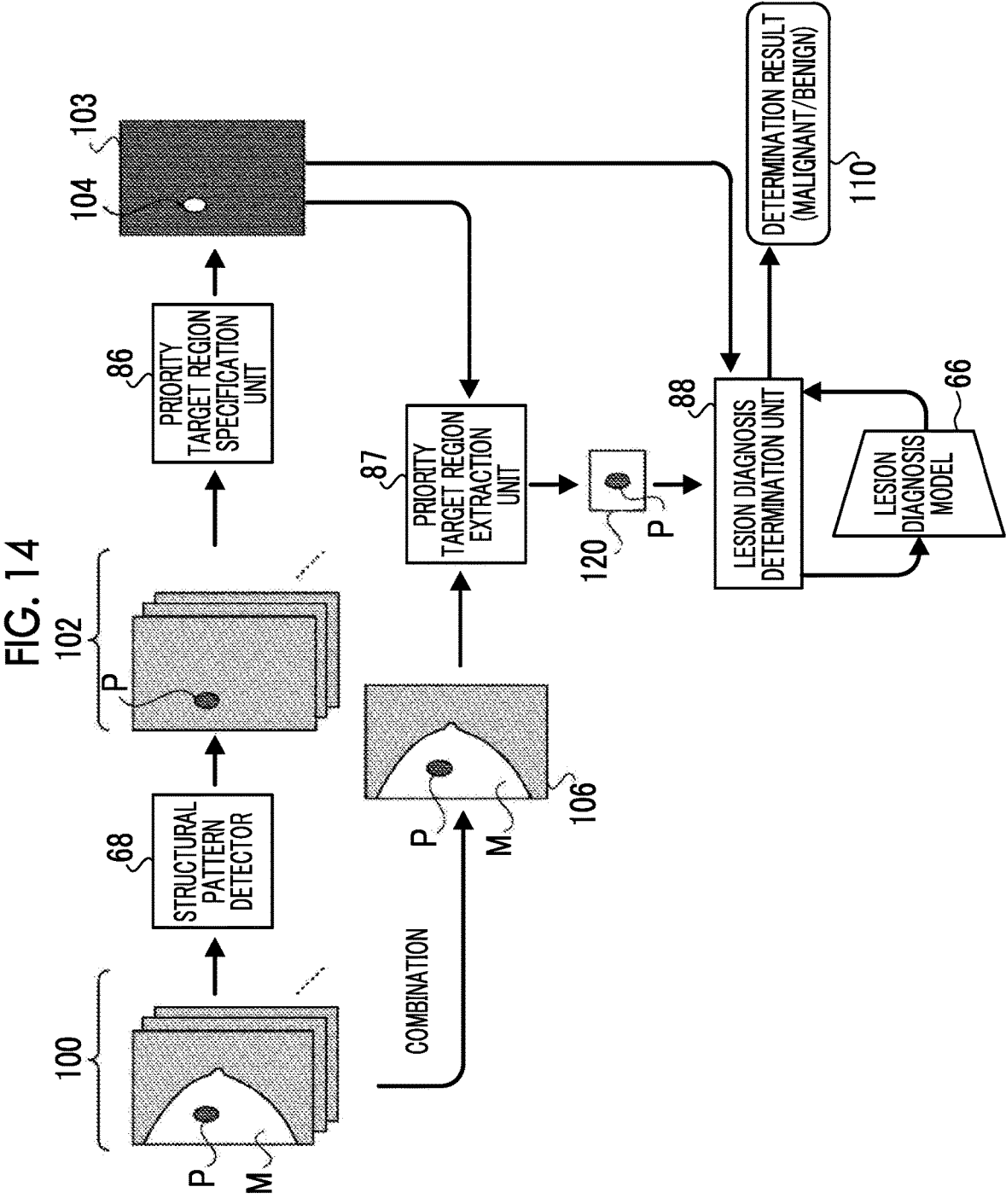
FIG. 14 is a schematic diagram illustrating an outline of a flow of determination regarding a diagnosis of a lesion in an image processing device according to Modification Example 1.

FIG. 14 is a schematic diagram illustrating the outline of the flow of the determination of the lesion diagnosis model 66 in the image processing device 16 according to this modification example.

In the above-described embodiment, the aspect has been described in which the entire synthesized two-dimensional image 106 is input to the lesion diagnosis model 66 and the lesion diagnosis model 66 performs the determination regarding the diagnosis of the lesion on the entire synthesized two-dimensional image 106. In contrast, in this modification example, as illustrated in FIG. 14, the priority target region 104 is extracted from the synthesized two-dimensional image 106 and is cut out as a patch 120. The patch 120 is input to the lesion diagnosis model 66, and the lesion diagnosis model 66 performs the determination regarding the diagnosis of the lesion on the patch 120.

Figure 15:
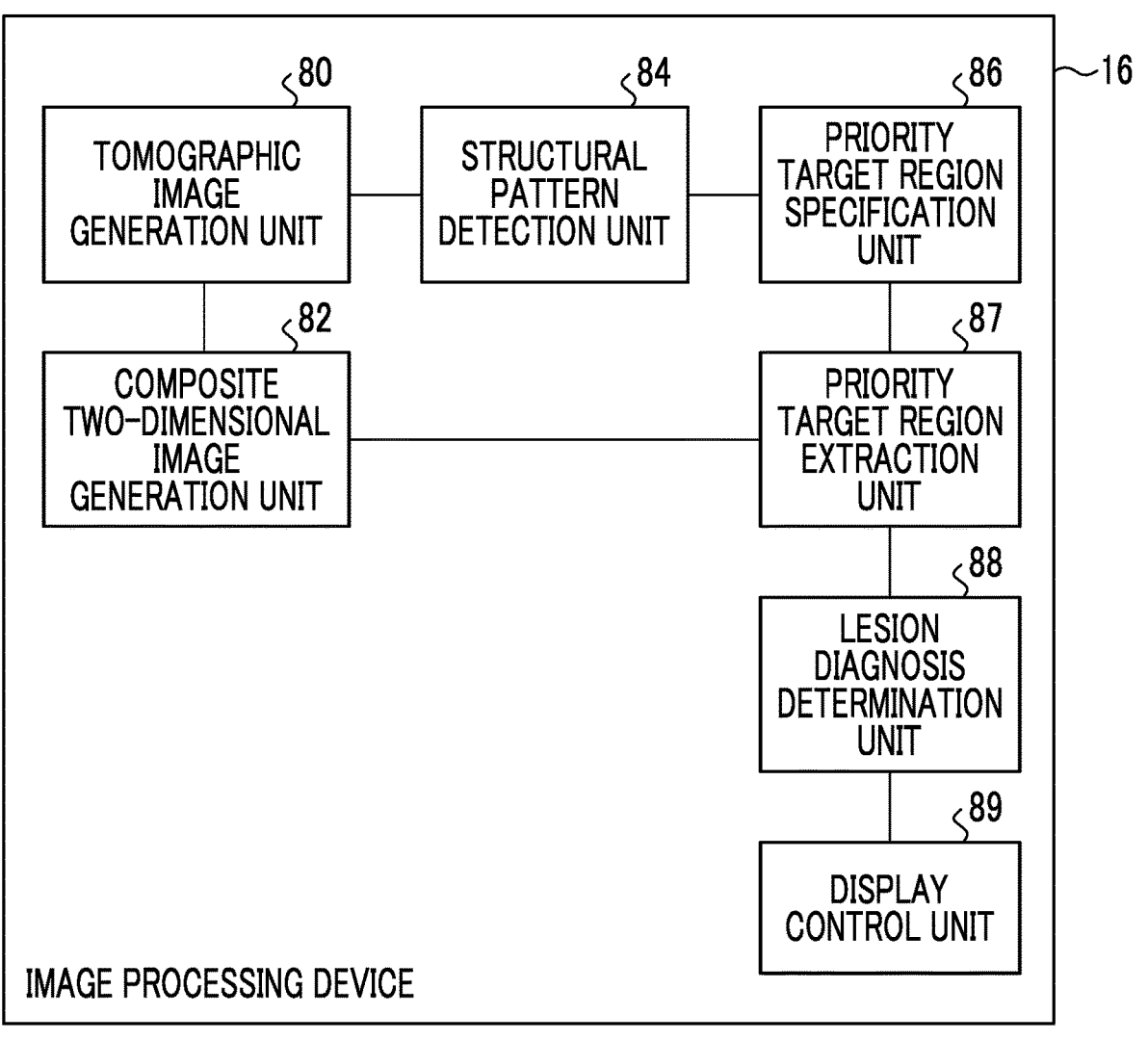
FIG. 15 is a functional block diagram illustrating an example of a configuration related to a function of performing the determination regarding the diagnosis of the lesion in the image processing device according to Modification Example 1.

FIG. 15 is a functional block diagram illustrating an example of a configuration related to a function of performing the determination regarding the diagnosis of the lesion in the image processing device 16 according to this modification example. As illustrated in FIG. 15, the image processing device 16 according to this modification example is different from the image processing device 16 (see FIG. 10) according to the above-described embodiment in that it comprises a priority target region extraction unit 87.

In the image processing device 16, the CPU 60A of the control unit 60 executes the image processing program 63B stored in the storage unit 62 to further function as the priority target region extraction unit 87.

The synthesized two-dimensional image 106 generated by the synthesized two-dimensional image generation unit 82 and the mask image 103 indicating the priority target region 104 specified by the priority target region specification unit 86 are input to the priority target region extraction unit 87. The priority target region extraction unit 87 has a function of extracting the priority target region 104 from the synthesized two-dimensional image 106 on the basis of the mask image 103 indicating the priority target region 104. In other words, the priority target region extraction unit 87 cuts out the patch 120 including the priority target region 104 from the synthesized two-dimensional image 106 on the basis of the mask image 103. The priority target region extraction unit 87 outputs the cut-out patch 120 to the lesion diagnosis determination unit 88.

The lesion diagnosis determination unit 88 inputs the cut-out priority target region 104 to the lesion diagnosis model 66 and acquires the determination result 110 output from the lesion diagnosis model 66.

Figure 16:
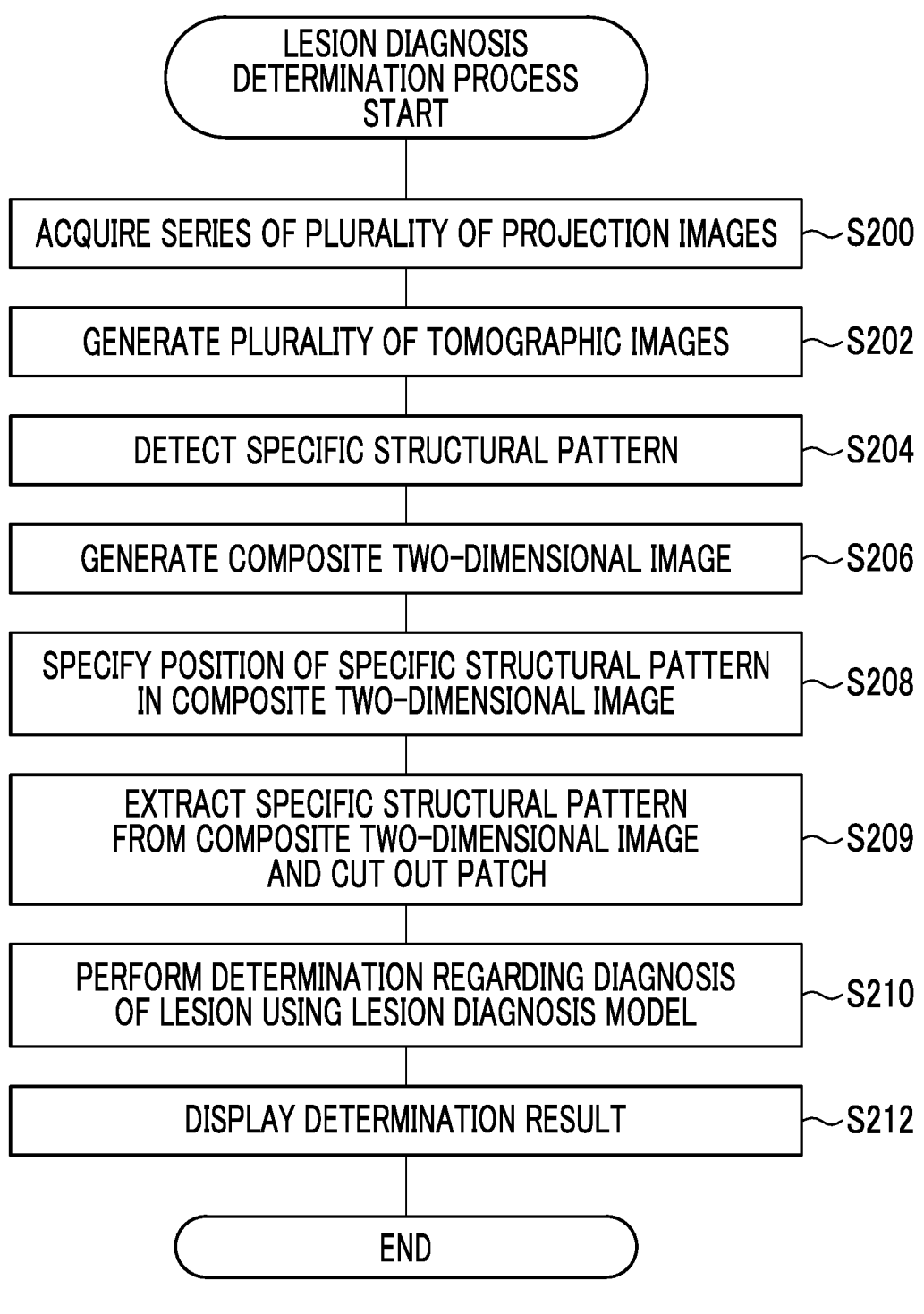
FIG. 16 is a flowchart illustrating an example of a flow of a lesion diagnosis determination process by the image processing device according to Modification Example 1.

FIG. 16 is a flowchart illustrating an example of the flow of a lesion diagnosis determination process by the image processing device 16 according to this modification example. The lesion diagnosis determination process illustrated in FIG. 16 is different from the lesion diagnosis determination process (see FIG. 12) according to the above-described embodiment in that it comprises Step S209 between Steps S208 and S210.

As illustrated in FIG. 16, in Step S209, the priority target region extraction unit 87 extracts the priority target region 104 from the synthesized two-dimensional image 106 on the basis of the mask image 103 indicating the priority target region 104 specified in Step S208 and cuts out the patch 120 as described above.

As a result, as described above, in Step S210, the lesion diagnosis determination unit 88 inputs the patch 120 cut out in Step S209 to the lesion diagnosis model 66, acquires the determination result output from the lesion diagnosis model 66, and outputs the determination result 110 as in the lesion diagnosis determination process (see FIG. 12) as described above.

As described above, in this modification example, the patch 120 including the priority target region 104 is cut out from the synthesized two-dimensional image 106, and instead of the entire synthesized two-dimensional image 106, the cut-out patch 120 is input to the lesion diagnosis model 66 to perform the determination based on the diagnosis of the lesion. Therefore, the amount of processing in the lesion diagnosis model 66 can be less than that in a case in which the entire synthesized two-dimensional image 106 is input to the lesion diagnosis model 66 to perform the determination regarding the diagnosis of the lesion. As a result, it is possible to suppress an increase in so-called calculation cost.

MODIFICATION EXAMPLE 2

Modification Example of Detection of Specific
Structural Pattern

A modification example of the detection of the specific structural pattern P from a plurality of tomographic images 100 in the image processing device 16 according to this modification example will be described.

There are a plurality of types of specific structural patterns P for lesions. For example, since the shape of the lesion differs depending on the type, there are types corresponding to the shapes of the lesions. Specifically, in a case in which the lesion is a tumor, the specific structural pattern P tends to have a spherical shape. In a case in which the lesion is a spicula, the specific structural pattern P tends to have a radial shape. Therefore, in this modification example, an aspect in which the specific structural pattern P is detected according to the type of the specific structural pattern P will be described.

Figure 17:
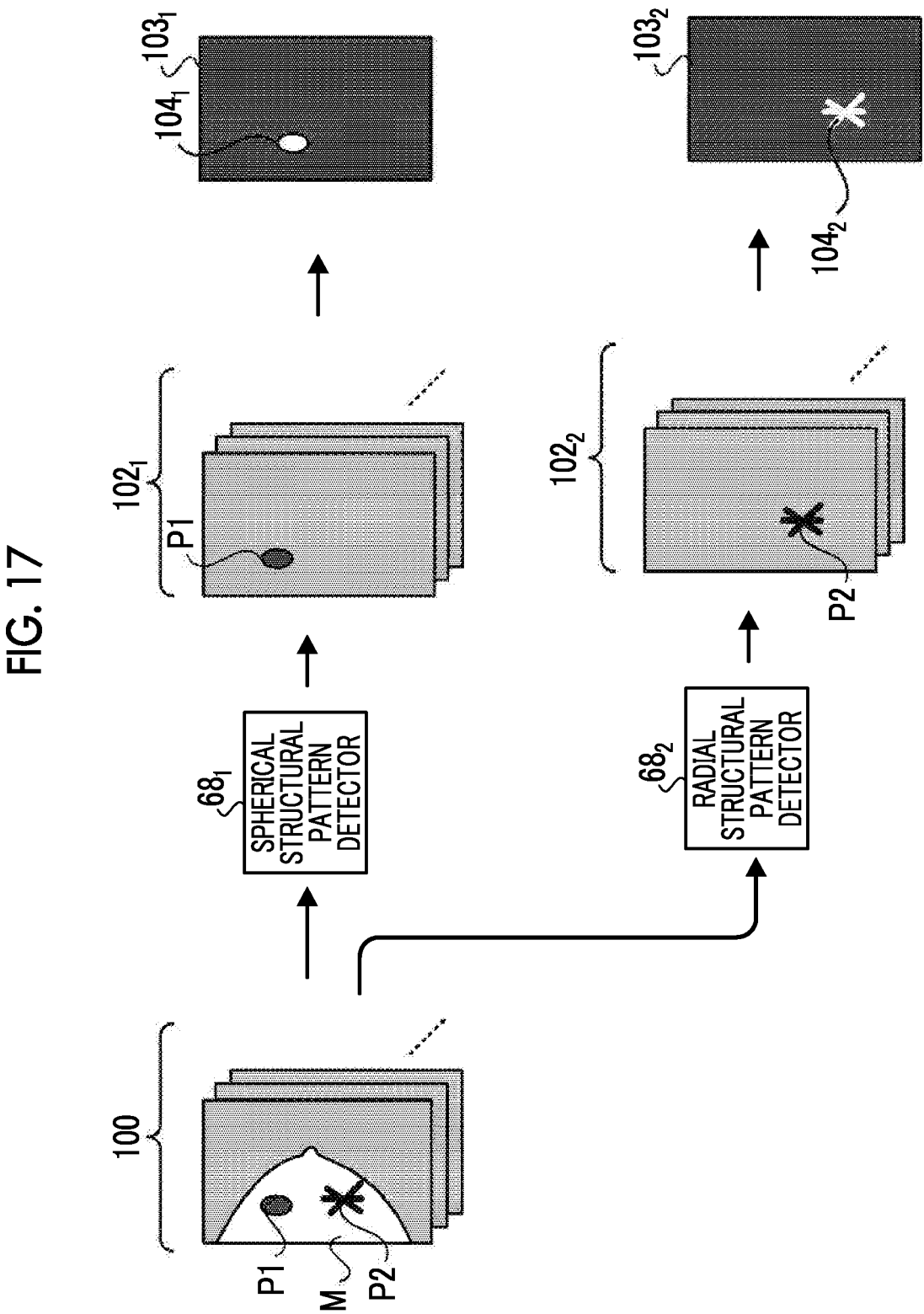
FIG. 17 is a schematic diagram illustrating an outline of a flow of determination regarding a diagnosis of a lesion in an image processing device according to Modification Example 2.
Figure 18:
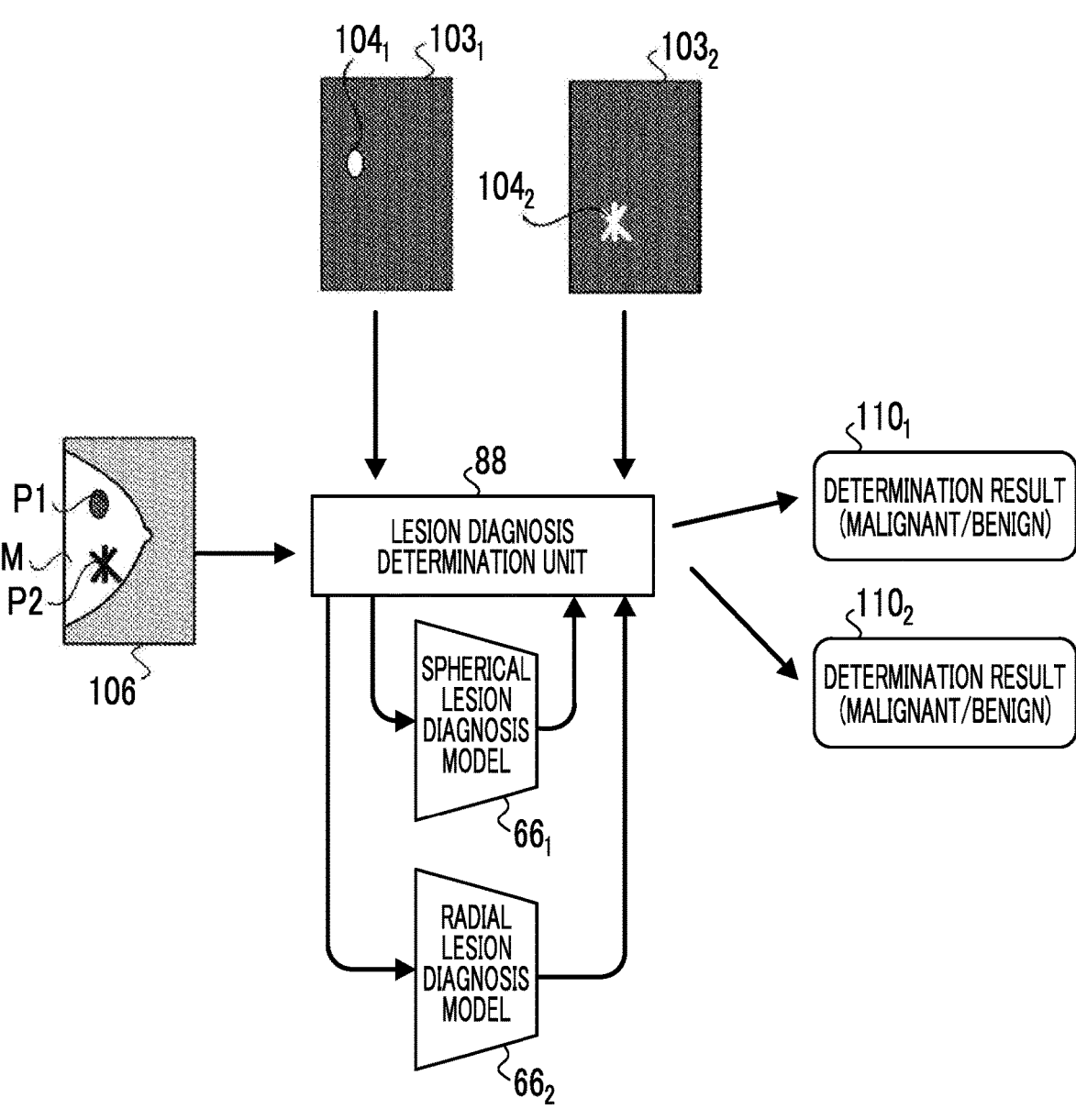
FIG. 18 is a schematic diagram illustrating an outline of a flow of determination regarding a diagnosis of a lesion in an image processing device according to Modification Example 3.
Figure 19:
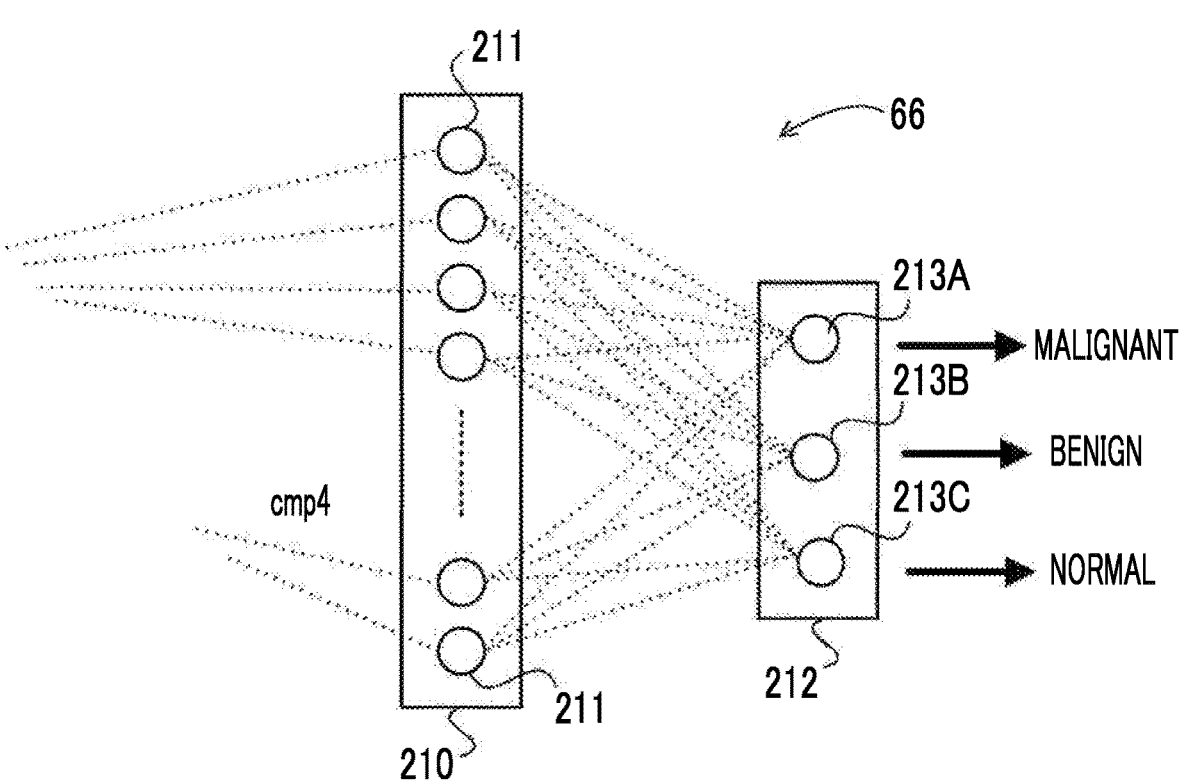
FIG. 19 is a diagram illustrating a determination result by a lesion diagnosis model in Modification Example 4.

FIG. 17 is a schematic diagram illustrating the outline of the flow of the detection of the specific structural pattern P in the image processing device 16 according to this modification example. In the example illustrated in FIG. 17, a specific structural pattern P1 of a tumor and a specific structural pattern P2 of a spicula are detected. Specifically, the structural pattern detection unit 84 detects the specific structural pattern P1 of the tumor from each of a plurality of tomographic images $100$ using a spherical structural pattern detector $68_1$ and generates a mask image $102_1$ corresponding to the specific structural pattern P1 which is the tumor. In addition, the structural pattern detection unit $84$ detects the specific structural pattern P2 of the spicula from each of the plurality of tomographic images $100$ using a radial structural pattern detector $68_2$ and generates a mask image $102_2$ corresponding to the specific structural pattern P2 which is the spicula.

Further, in the example illustrated in FIG. $17$, a mask image $103_1$ indicating a priority target region $104_1$ including the specific structural pattern P having a spherical shape specified by the priority target region specification unit $86$ is generated from the mask image $102_1$. Furthermore, a mask image $103_2$ indicating a priority target region $104_2$ including the specific structural pattern P having a radial shape specified by the priority target region specification unit $86$ is generated from a mask image $102_2$.

In addition, the present disclosure is not limited to the example illustrated in FIG. $17$. For example, the mask images $102_1$ and $102_2$ may be integrated to generate a mask image $102$, and the priority target region specification unit $86$ may specify the priority target region $104$, in which the specific structural pattern P is present, in the synthesized two-dimensional image $106$ on the basis of the integrated mask image $102$.

As described above, in this modification example, the structural pattern detector $68$ corresponding to the type of the specific structural pattern P is used. Therefore, it is possible to increase the accuracy of detecting the specific structural pattern P. In addition, it is possible to determine the type of the specific structural pattern P included in the breast M.

In addition, in a case in which the type of the specific structural pattern P, that is, the type of the lesion, is specified in this way, it is possible to extract the size of the priority target region $104$ including the specific structural pattern P under the conditions corresponding to the type or to detect the priority target region $104$ according to the type. For example, the influence on the surroundings of the lesion may differ depending on the type of the lesion. Therefore, for example, a range that is extracted as the priority target region $104$ may be changed depending on the type of the specific structural pattern P on the basis of these conditions.

Further, the lesion diagnosis model $66$ may be used to perform the determination regarding the diagnosis of the lesion for each type of the specific structural pattern P, that is, for each type of lesion.

MODIFICATION EXAMPLE 3

Modification Example of Determination Regarding Diagnosis of Lesion

A modification example of the determination regarding the diagnosis of the lesion in the image processing device $16$ according to this modification example will be described.

As described in Modification Example 2, there are a plurality of types of specific structural patterns P corresponding to the shapes of lesions. Therefore, in this modification example, an aspect in which the lesion diagnosis model $66$ corresponding to the type of the specific structural pattern P is used to perform the determination regarding the diagnosis of the lesion will be described.

FIG. $18$ is a schematic diagram illustrating the outline of the flow of the determination regarding the diagnosis of the lesion in the image processing device $16$ according to this modification example. In the example illustrated in FIG. $18$, the lesion diagnosis determination unit $88$ outputs a determination result $110_1$ for a spherical lesion included in the synthesized two-dimensional image $106$ on the basis of the mask image $103_1$ indicating the priority target region $104_1$, in which the specific structural pattern P1 having a spherical shape is present, using a spherical lesion diagnosis model $66_1$ subjected to machine learning for the determination regarding the diagnosis of the spherical lesion such as a tumor. In addition, the lesion diagnosis determination unit $88$ outputs a determination result $110_2$ for a radial lesion included in the synthesized two-dimensional image $106$ on the basis of the mask image $103_2$ indicating the priority target region $104_2$, in which the specific structural pattern P2 having a radial shape is present, using a radial lesion diagnosis model $66_2$ subjected to machine learning for the determination regarding the diagnosis of the radial lesion such as a spicula.

As described above, in this modification example, in the determination regarding the diagnosis of the lesion, the determination corresponding to the type of the specific structural pattern P, that is, the type of the lesion, is performed. Therefore, it is possible to further increase the accuracy of determination.

In addition, in this modification example, the aspect in which the determination result $110$ is output for each type of lesion, that is, each type of the specific structural pattern P, has been described. However, the present disclosure is not limited to this modification example, and the determination result $110$ of integrating the diagnosis of all of the lesions may be output.

MODIFICATION EXAMPLE 4

Modification Example of Determination Result

In the above-described embodiment, the aspect in which whether the lesion is "malignant" or "benign" is output as the determination result $110$ output by the lesion diagnosis determination unit $88$ has been described. However, the determination result $110$ output by the lesion diagnosis determination unit $88$ is not limited thereto. In other words, in the above-described embodiment, the aspect in which whether the lesion is "malignant" or "benign" is output as the determination result output by the lesion diagnosis model $66$ has been described. However, the determination result output by the lesion diagnosis model $66$ is not limited thereto.

For example, in a case in which the mammary glands overlap, they look like a radial structure. Therefore, the mammary glands may be mistaken for a spicula and may be detected by the structural pattern detector $68$. In this case, the mammary glands may be determined to be "normal" rather than "malignant" or "benign". In this case, in the lesion diagnosis model $66$, for example, as illustrated in FIG. $19$, the output layer $212$ of the lesion diagnosis model $66$ has a node $213A$ corresponding to the determination that the lesion is malignant, a node $213B$ corresponding to the determination that the lesion is benign, and a node $213C$ corresponding to the determination that the specific structural pattern is not a lesion (normal). Then, the establishment of each of the nodes $213A$ to $213C$ may be derived, and the determination associated with a node having the highest probability may be output as the determination result, or the probability of each of the nodes $213A$ to $213C$ may be output as the determination result.

Further, how to process the determination result 110 output by the lesion diagnosis determination unit 88 and the determination result output from the lesion diagnosis model 66 as described above is not limited. For example, in some cases, the shape of the lesion changes depending on the degree of malignancy, for example, the progress of cancer. In this case, the lesion diagnosis determination unit 88 may output the determination result 110 indicating the degree of malignancy using the lesion diagnosis model 66 that can obtain the determination result of the degree of malignancy of the lesion.

Further, for example, the lesion diagnosis determination unit 88 may output the determination result 110 indicating whether or not the specific structural pattern P detected as a lesion candidate structure is a lesion, using the lesion diagnosis model 66 that can obtain the result of the determination of whether or not the specific structural pattern P is a lesion. In this case, for example, the node 213A of the output layer 212 (see FIG. 5) of the lesion diagnosis model 66 may be used as a node corresponding to the determination that the specific structural pattern P is a lesion, and the node 213B may be used as a node corresponding to the determination that the specific structural pattern P is not a lesion (normal).

Furthermore, for example, the lesion diagnosis determination unit 88 may output the determination result 110 indicating whether or not the specific structural pattern P detected as the lesion candidate structure is a malignant lesion, using the lesion diagnosis model 66 that can obtain the result of the determination of whether or not the specific structural pattern P is a lesion. In this case, for example, the node 213A of the output layer 212 (see FIG. 5) of the lesion diagnosis model 66 may be used as a node corresponding to the determination that the specific structural pattern P is a malignant lesion, and the node 213B may be used as a node corresponding to the determination that the specific structural pattern P is not a malignant lesion or that the specific structural pattern P is not a lesion (normal).

MODIFICATION EXAMPLE 5

Modification Example of Specification of Priority Target Region

In this modification example, a modification example of the specification of the priority target region 104 will be described.

Figure 20:
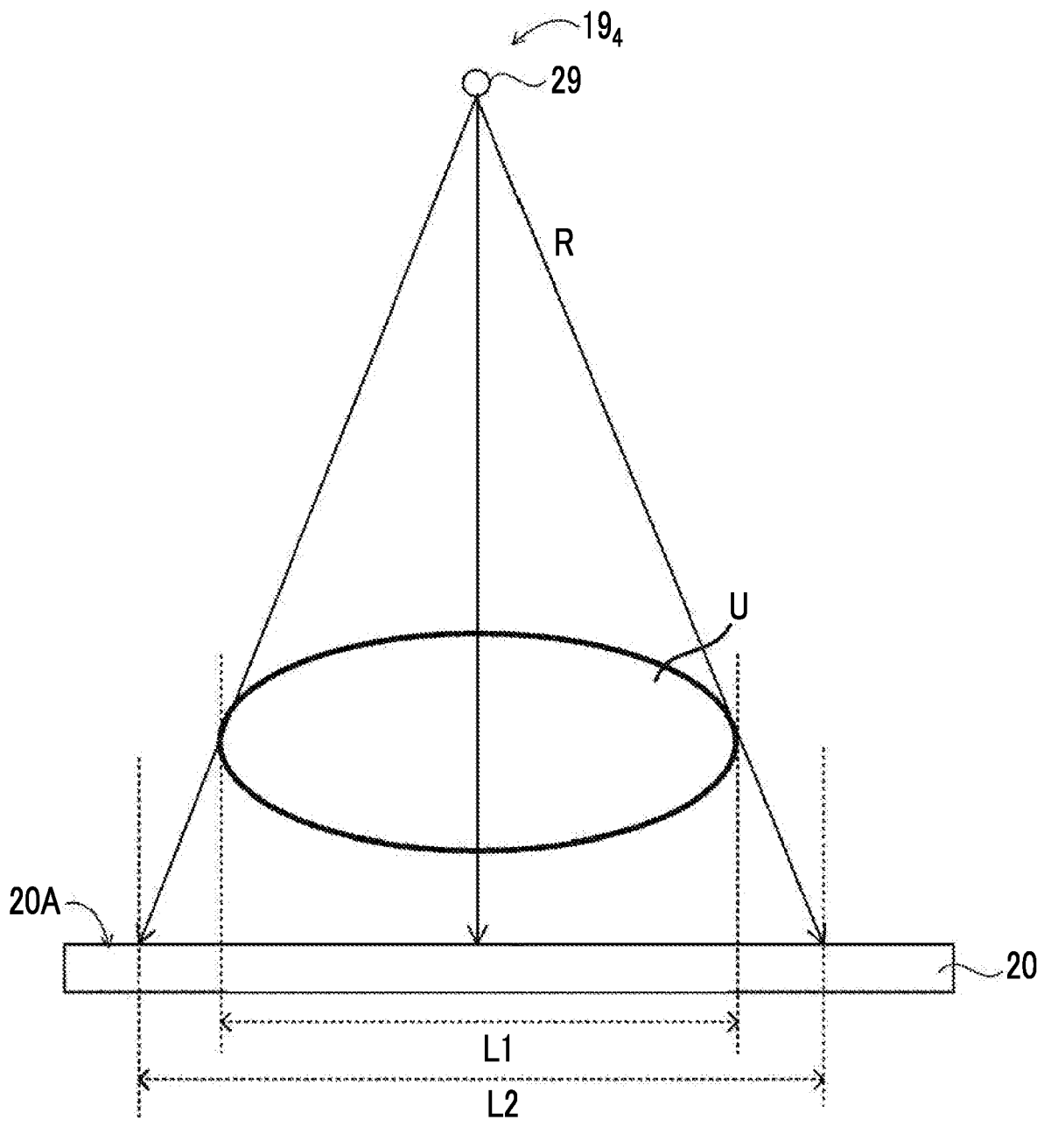
FIG. 20 is a diagram illustrating size correction in Modification Example 5.

In some cases, the size of the breast M in a plurality of tomographic images 100 is different from the size of the breast M in the synthesized two-dimensional image 106. As illustrated in FIG. 20, the size of the breast M in the plurality of tomographic images 100 and in the synthesized two-dimensional image 106 is determined according to the positional relationship among the radiation source 29, the breast U, and the detection surface 20A of the radiation detector 20. For example, in the example illustrated in FIG. 20, the size of the breast M included in each of the plurality of tomographic images 100 is a length L1 corresponding to the distance from one end to the other end of the breast U in a plane parallel to the detection surface 20A of the radiation detector 20. On the other hand, the size of the breast M included in the synthesized two-dimensional image 106 is a length L2 corresponding to the distance between contact points between straight lines connecting the radiation source 29 and the ends of the breast U and the detection surface 20A of the radiation detector 20. As described above, in the example illustrated in FIG. 20, the size of the breast M included in the synthesized two-dimensional image 106 is larger than the size of the breast M included in each of the plurality of tomographic images 100.

As described above, since the size of the breast M included in each of the plurality of tomographic images 100 is different from the size of the breast M included in the synthesized two-dimensional image 106, correction for making the sizes of the breast M equal to each other (hereinafter referred to as "size correction") may be performed.

Therefore, in a case in which the size correction is performed on at least one of the plurality of tomographic images 100 or the synthesized two-dimensional image 106, the priority target region specification unit 86 specifies the priority target region 104, in which the specific structural pattern P is present, in the synthesized two-dimensional image 106 using the plurality of tomographic images 100 and the synthesized two-dimensional image 106 without any change.

On the other hand, in a case in which the size correction is not performed, the priority target region specification unit 86 performs correction corresponding to the size correction on the priority target region 104, in which the specific structural pattern P is present, in the synthesized two-dimensional image 106. For example, the priority target region specification unit 86 may project the position (coordinates) of the specific structural pattern P (priority target region 104) in each of the plurality of tomographic images 100 on the basis of the position (coordinates) of the radiation source 29 and derive the position (coordinates) of the specific structural pattern P (priority target region 104) in the synthesized two-dimensional image 106. Further, for example, the priority target region specification unit 86 may project the mask images 102 corresponding to the plurality of tomographic images 100 on the basis of the position (coordinates) of the radiation source 29 and derive the position (coordinates) of the specific structural pattern P (priority target region 104) in the synthesized two-dimensional image 106. Furthermore, for example, the priority target region specification unit 86 may project a multi-valued image indicating the likelihood corresponding to the plurality of tomographic images 100 on the basis of the position (coordinates) of the radiation source 29, acquire a multi-valued image indicating the likelihood in the synthesized two-dimensional image 106, and derive a region that is equal to or greater than a threshold value as the specific structural pattern P (priority target region 104) in the synthesized two-dimensional image 106.

MODIFICATION EXAMPLE 6

Modification Example of Determination Method in Lesion Diagnosis Determination Unit 88

A modification example in which the lesion diagnosis determination unit 88 focuses the determination regarding the diagnosis of the lesion on the priority target region 104 will be described with reference to FIG. 21. In the example illustrated in FIG. 21, a modification example of a case in which the lesion diagnosis model 66 using a sliding window method changes a method for sliding a window 122 to focus the determination regarding the diagnosis of the lesion on the priority target region 104 is described.

Figure 21:
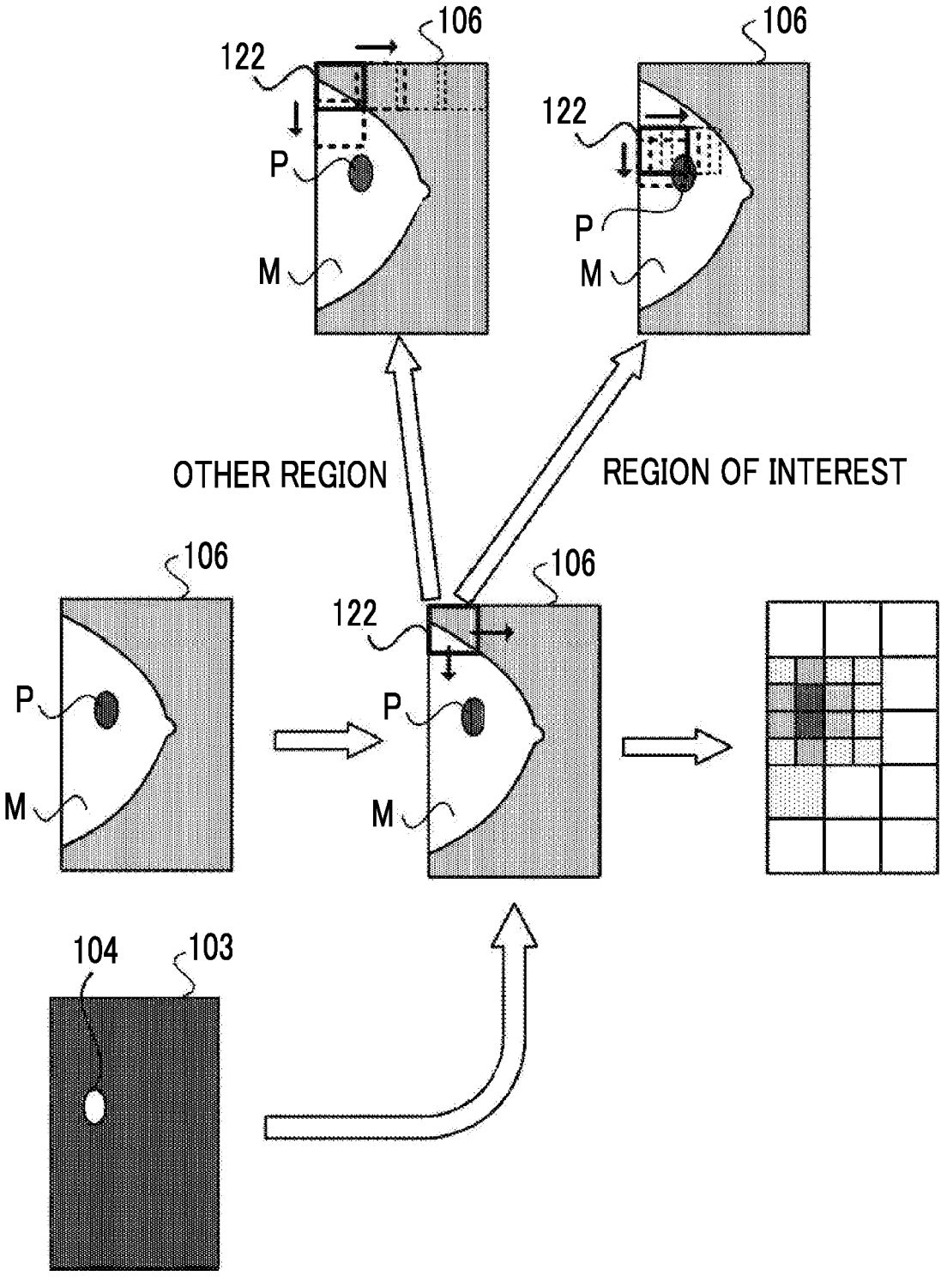
FIG. 21 is a diagram illustrating an example of a determination method by a lesion diagnosis determination unit according to Modification Example 6.

As illustrated in FIG. 21, the lesion diagnosis determination unit 88 sets the slide width of the window 122, which scans (slides) the synthesized two-dimensional image 106, in the priority target region 104 to be smaller than that in the other region and applies the lesion diagnosis model 66. As described above, since the slide width is reduced, the number of determination operations on the priority target region 104 can be larger than the number of determination operations on the other region, and it is possible to focus the determination regarding the diagnosis of the lesion on the priority target region 104.

In addition, the present disclosure is not limited to this modification example. For example, for the window 122 in the lesion diagnosis model 66, the lesion diagnosis determination unit 88 may set the window 122 in the priority target region 104 to be smaller than the window 122 in the other region such that the number of determination operations on the priority target region 104 is larger than the number of determination operations on the other region.

Further, in the above-described embodiment, the aspect in which the specific structural pattern P is detected from a plurality of tomographic images 100 has been described. However, the image from which the specific structural pattern P to be detected is not limited to the plurality of tomographic images 100 and may be a series of a plurality of projection images used to obtain the plurality of tomographic images 100.

As described above, the image processing device 16 according to the above-described embodiment comprises the CPU 60A, and the CPU 60A detects the specific structural pattern P indicating a lesion candidate structure for the breast U in a series of a plurality of projection images obtained by performing the tomosynthesis imaging on the breast U or in a plurality of tomographic images 100 obtained from the plurality of projection images. Further, the CPU 60A synthesizes the plurality of tomographic images 100 to generate the synthesized two-dimensional image 106, specifies the priority target region 104, in which the specific structural pattern P is present, in the synthesized two-dimensional image 106, and performs the determination regarding the diagnosis of the lesion on the basis of the synthesized two-dimensional image 106 and the priority target region 104.

In the synthesized two-dimensional image 106, it may be difficult to detect the specific structural pattern P because tissues, such as mammary glands, overlap or are hidden behind normal tissues. In contrast, in the above-described embodiment, since the specific structural pattern P is detected from a series of a plurality of projection images or from a plurality of tomographic images 100, it is easy to detect the specific structural pattern P. Further, only the determination regarding the diagnosis of the lesion is performed on the specific structural pattern P detected as a lesion from the synthesized two-dimensional image 106. Therefore, it is possible to specialize in the determination regarding the diagnosis of the lesion. Therefore, according to the image processing device 16 of the above-described embodiment, it is possible to accurately perform determination regarding the diagnosis of a lesion of the breast.

In addition, a method for detecting the specific structural pattern P is not limited to the method to which the CAD algorithm based on the probability of being the specific structural pattern P is applied. For example, the specific structural pattern P may be detected from a plurality of tomographic images 100 by a filtering process with a filter for detecting the specific structural pattern P, a detection model subjected to machine learning by deep learning or the like to detect the specific structural pattern P, and the like. Further, a trained model that has been trained by machine learning may be used as the structural pattern detector 68. As a model applied as the structural pattern detector 68, a classification method using a convolutional neural network (CNN), such as ResNet, is applied by the sliding window method. Alternatively, various machine learning models including a segmentation method, such as U-Net, and an object-detection method, such as Faster-RCNN, are assumed. In addition, for example, a multilayer perceptron (MLP) may be applied. Further, for example, the following can be applied: a structural pattern detector 68 generated by performing machine learning on a machine learning model with a geometrical structural pattern; a structural pattern detector 68 generated by performing machine learning on a mathematical model with simulation image data; and a structural pattern detector 68 generated by performing machine learning on a machine learning model using a radiographic image of a breast as training data.

Furthermore, in the above-described embodiment, the aspect in which the lesion diagnosis model 66 is applied to the synthesized two-dimensional image 106 to perform the determination regarding the diagnosis of the lesion, regardless of the detection result of the structural pattern detection unit 84, has been described. However, whether or not to perform the determination regarding the diagnosis of the lesion to which the lesion diagnosis model 66 is applied may differ depending on the detection result of the structural pattern detection unit 84. For example, in a case in which the structural pattern detector 68 detects a specific structural pattern P for a lesion that can be said to be definitely malignant or a lesion that can be said to be definitely benign, the determination regarding the diagnosis of the lesion to which the lesion diagnosis model 66 is applied may not be performed, and the determination regarding the diagnosis of the lesion may be performed on the basis of the detection result of the structural pattern detector 68.

Further, as described above, in addition to the classification method using a convolutional neural network (CNN), such as ResNet, for example, the multilayer perceptron (MLP) may be applied as the lesion diagnosis model 66.

Figure 22:
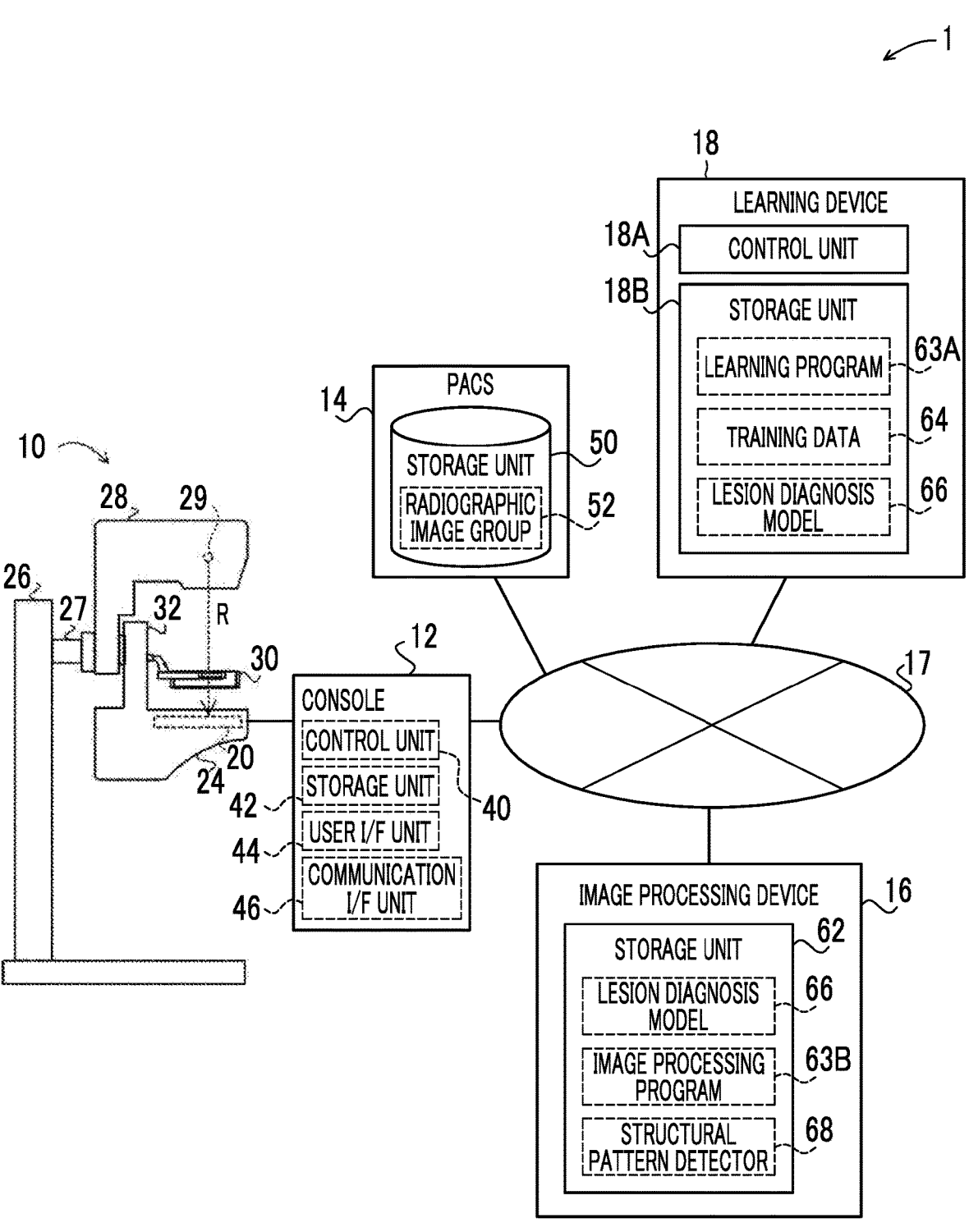
FIG. 22 is a diagram schematically illustrating another example of the overall configuration of the radiography system according to the embodiment.

In addition, in the above-described embodiment, the aspect has been described in which the image processing device 16 trains the lesion diagnosis model 66 and performs the determination regarding the diagnosis of the lesion using the lesion diagnosis model 66. However, a learning device other than the image processing device 16 may train the lesion diagnosis model 66. That is, a device that trains the lesion diagnosis model 66 may be different from a device that performs the determination regarding the diagnosis of the lesion using the lesion diagnosis model 66. FIG. 22 is a diagram schematically illustrating an example of the overall configuration of a radiography system 1 in a case in which a learning device 18 other than the image processing device 16 trains the lesion diagnosis model 66. The radiography system 1 illustrated in FIG. 22 further comprises the learning device 18. An example of the learning device 18 is a computer system comprising a control unit 18A and a storage unit 18B such as a central processing unit (CPU), a read only memory (ROM), and a random access memory (RAM). The learning program 63A, the training data 64, and the lesion diagnosis model 66 included in the storage unit 62 of the image processing device 16 according to the above-described embodiment are stored in the storage unit 18B. The learning device 18 executes the learning program 63A using the control unit 18A to perform training with the training data 64, thereby generating the lesion diagnosis model 66. The lesion diagnosis model 66 generated by the learning device 18 is transmitted to the image processing device 16 and is stored in the storage unit 62 of the image processing device 16. In this case, unlike the image processing device 16 (see FIG. 3) according to the above-described embodiment, the learning program 63A and the training data 64 may not be stored in the storage unit 62 of the image processing device 16.

Furthermore, in the above-described embodiment, for example, the following various processors can be used as a hardware structure of processing units performing various processes, such as the tomographic image generation unit 80, the synthesized two-dimensional image generation unit 82, the structural pattern detection unit 84, the priority target region specification unit 86, the lesion diagnosis determination unit 88, and the display control unit 89 and a hardware structure of processing units performing various processes, such as the training data acquisition unit 90 and the lesion diagnosis model generation unit 92. The various processors include, for example, a programmable logic device (PLD), such as a field programmable gate array (FPGA), that is a processor whose circuit configuration can be changed after manufacture, and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the learning program 63A and the image processing program 63B are stored (installed) in the storage unit 62 in advance has been described. However, the present disclosure is not limited thereto. Each of the learning program 63A and the image processing program 63B may be recorded on a recording medium, such as a compact disc read only memory (CD-ROM), a digital versatile disc read only memory (DVD-ROM), or a universal serial bus (USB) memory, and then be provided. Furthermore, each of the learning program 63A and the image processing program 63B may be downloaded from an external device through the network.

What is claimed is:

1. An image processing device comprising at least one processor, wherein the processor:

detects a specific structural pattern indicating a lesion candidate structure for a breast in a series of a plurality of projection images obtained by performing tomosynthesis imaging on the breast or in a plurality of tomographic images obtained from the plurality of projection images, synthesizes the plurality of tomographic images to generate a synthesized two-dimensional image, specifies a priority target region, in which the specific structural pattern is present, in the synthesized two-dimensional image, performs determination regarding a diagnosis of a lesion on the basis of the synthesized two-dimensional image and the priority target region, generates a likelihood map indicating a probability that the lesion is malignant for the entire synthesized two-dimensional image, generates a weight map in which a weight for the priority target region is larger than a weight for another region in the synthesized two-dimensional image, performs the determination regarding the diagnosis of the lesion by multiplying a likelihood in the likelihood map by the weight in the weight map for each corresponding region, and makes a number of performing the determination regarding the diagnosis of the lesion on the priority target region larger than that on the other region in the synthesized two-dimensional image.

2. The image processing device according to claim 1, wherein the processor focuses the determination regarding the diagnosis of the lesion more on the priority target region than on the other region in the synthesized two-dimensional image.

3. The image processing device according to claim 1, wherein the processor extracts the priority target region from the synthesized two-dimensional image and performs the determination regarding the diagnosis of the lesion on the extracted priority target region.

4. The image processing device according to claim 3, wherein the processor extracts the priority target region on the basis of a condition corresponding to a type of the specific structural pattern.

5. The image processing device according to claim 1, wherein the processor detects the specific structural pattern for a type of the specific structural pattern.

6. The image processing device according to claim 1, wherein the processor specifies a type of the specific structural pattern and specifies the priority target region for a specified type.

7. The image processing device according to claim 1, wherein the processor specifies a type of the specific structural pattern and performs the determination regarding the diagnosis of the lesion on the basis of the specified type and the priority target region.

8. The image processing device according to claim 7, wherein the processor determines whether the lesion is benign or malignant as the determination regarding the diagnosis of the lesion.

9. The image processing device according to claim 7, wherein the processor determines whether or not the specific structural pattern is a lesion as the determination regarding the diagnosis of the lesion.

10. The image processing device according to claim 7, wherein the processor determines whether or not the lesion is malignant as the determination regarding the diagnosis of the lesion.

11. The image processing device according to claim 7, wherein the processor determines whether the specific structural pattern is a benign lesion, a malignant lesion, or a structure other than a lesion as the determination regarding the diagnosis of the lesion.

12. The image processing device according to claim 7, wherein the processor determines a degree of malignancy as the determination regarding the diagnosis of the lesion.

13. The image processing device according to claim 1, wherein the processor specifies a type of the specific structural pattern using a plurality of detectors that are provided for multiple types of specific structural patterns and outputs, as a detection result, information indicating the specific structural pattern from the plurality of projection images or from the plurality of tomographic images.

14. The image processing device according to claim 1, wherein the processor detects the specific structural pattern using a detector generated by performing machine learning on a machine learning model with a geometrical structural pattern, a detector generated by performing machine learning on a mathematical model with simulation image data, or a detector generated by performing machine learning on a machine learning model using a radiographic image of the breast as training data.

15. The image processing device according to claim 1, wherein, in a case in which a size of the breast included in the plurality of tomographic images is different from a size of the breast included in the synthesized two-dimensional image, the processor performs a process of making the sizes equal to each other to specify the priority target region, in which the specific structural pattern is present, in the synthesized two-dimensional image.

16. The image processing device according to claim 1, wherein a process of specifying the priority target region, in which the specific structural pattern is present, in the synthesized two-dimensional image is incorporated into a process of synthesizing the plurality of tomographic images to generate the synthesized two-dimensional image.

17. The image processing device according to claim 1, wherein the processor sets a window, which scans the synthesized two-dimensional image, or a slide width of the window in the priority target region to be smaller than that in the other region in the synthesized two-dimensional image.

18. The image processing device according to claim 1, wherein the processor:
  generates a plurality of first mask images in which a position of the specific structural pattern is shown,
  generates a second mask image indicating the priority target region, by use of the plurality of first mask images, and
  performs the determination regarding the diagnosis of the lesion on the basis of the synthesized two-dimensional image and the second mask image.

19. An image processing method executed by a computer, the image processing method comprising:
  detecting a specific structural pattern indicating a lesion candidate structure for a breast in a series of a plurality of projection images obtained by performing tomosynthesis imaging on the breast or in a plurality of tomographic images obtained from the plurality of projection images;

synthesizing the plurality of tomographic images to generate a synthesized two-dimensional image;

specifying a priority target region, in which the specific structural pattern is present, in the synthesized two-dimensional image;

performing determination regarding a diagnosis of a lesion on the basis of the synthesized two-dimensional image and the priority target region;

generating a likelihood map indicating a probability that the lesion is malignant for the entire synthesized two-dimensional image, generating a weight map in which a weight for the priority target region is larger than a weight for another region in the synthesized two-dimensional image, performing the determination regarding the diagnosis of the lesion by multiplying a likelihood in the likelihood map by the weight in the weight map for each corresponding region, and making a number of performing the determination regarding the diagnosis of the lesion on the priority target region larger than that on the other region in the synthesized two-dimensional image.

20. A non-transitory computer-readable storage medium storing an image processing program that causes a computer to execute a process comprising:
  detecting a specific structural pattern indicating a lesion candidate structure for a breast in a series of a plurality of projection images obtained by performing tomosynthesis imaging on the breast or in a plurality of tomographic images obtained from the plurality of projection images;
  synthesizing the plurality of tomographic images to generate a synthesized two-dimensional image;
  specifying a priority target region, in which the specific structural pattern is present, in the synthesized two-dimensional image;
  performing determination regarding a diagnosis of a lesion on the basis of the synthesized two-dimensional image and the priority target region;
  generating a likelihood map indicating a probability that the lesion is malignant for the entire synthesized two-dimensional image,
  generating a weight map in which a weight for the priority target region is larger than a weight for another region in the synthesized two-dimensional image,
  performing the determination regarding the diagnosis of the lesion by multiplying a likelihood in the likelihood map by the weight in the weight map for each corresponding region, and
  making a number of performing the determination regarding the diagnosis of the lesion on the priority target region larger than that on the other region in the synthesized two-dimensional image.

* * * * *